(12) United States Patent
Makriyannis et al.

(10) Patent No.: US 7,897,598 B2
(45) Date of Patent: *Mar. 1, 2011

(54) INHIBITORS OF THE ANANDAMIDE TRANSPORTER

(76) Inventors: Alexandros Makriyannis, Storrs, CT (US); Sonyuan Lin, Natick, MA (US); Daniele Piomelli, San Diego, CA (US)

( * ) Notice: Subject to any disclaimer, the term of this patent is extended or adjusted under 35 U.S.C. 154(b) by 292 days.

This patent is subject to a terminal disclaimer.

(21) Appl. No.: 09/328,742

(22) Filed: Jun. 6, 1999

(65) Prior Publication Data
US 2003/0149082 A1    Aug. 7, 2003

Related U.S. Application Data

(60) Provisional application No. 60/088,568, filed on Jun. 9, 1998.

(51) Int. Cl.
*A61K 31/535* (2006.01)
*A61K 31/445* (2006.01)
*A61K 31/21* (2006.01)
*A01N 43/76* (2006.01)
*A01N 37/02* (2006.01)

(52) U.S. Cl. ............ 514/231.2; 514/315; 514/376; 514/513; 514/546; 514/643

(58) Field of Classification Search ............ 514/310
See application file for complete search history.

(56) References Cited

U.S. PATENT DOCUMENTS

| | | |
|---|---|---|
| 3,041,343 A | 6/1962 | Jucker et al. |
| 3,465,024 A | 9/1969 | Brownstein et al. |
| 3,573,327 A | 3/1971 | Miyano |
| 3,577,458 A | 5/1971 | Brownstein et al. |
| 3,656,906 A | 4/1972 | Bullock |
| 3,838,131 A | 9/1974 | Gauthier |
| 3,886,184 A | 5/1975 | Matsumoto et al. |
| 3,897,306 A | 7/1975 | Vidic |
| 3,915,996 A | 10/1975 | Wright |
| 3,928,598 A | 12/1975 | Archer |
| 3,944,673 A | 3/1976 | Archer |
| 3,946,029 A | 3/1976 | Descamps et al. |
| 3,953,603 A | 4/1976 | Archer |
| 4,036,857 A | 7/1977 | Razdan et al. |
| 4,054,582 A | 10/1977 | Blanchard et al. |
| 4,087,545 A | 5/1978 | Archer et al. |
| 4,087,546 A | 5/1978 | Archer et al. |
| 4,087,547 A | 5/1978 | Archer et al. |
| 4,088,777 A | 5/1978 | Archer et al. |
| 4,102,902 A | 7/1978 | Archer et al. |
| 4,152,450 A | 5/1979 | Day et al. |
| 4,171,315 A | 10/1979 | Ryan et al. |
| 4,176,233 A | 11/1979 | Archer et al. |
| 4,179,517 A | 12/1979 | Mechoulam |
| 4,188,495 A | 2/1980 | Althuis et al. |
| 4,208,351 A | 6/1980 | Archer et al. |
| 4,278,603 A | 7/1981 | Thakkar et al. |
| 4,282,248 A | 8/1981 | Mechoulam et al. |
| 4,382,943 A | 5/1983 | Winter et al. |
| 4,395,560 A | 7/1983 | Ryan |
| 4,497,827 A * | 2/1985 | Nelson .................. 514/381 |
| 4,550,214 A | 10/1985 | Mehta |
| 4,758,597 A | 7/1988 | Martin et al. |
| 4,812,457 A | 3/1989 | Narumiya |
| 4,876,276 A | 10/1989 | Mechoulam |
| 4,885,295 A | 12/1989 | Bell et al. |
| 5,053,548 A | 10/1991 | Tanaka et al. |
| 5,068,234 A | 11/1991 | D'Ambra et al. |
| 5,147,876 A | 9/1992 | Mizuchi et al. |
| 5,223,510 A | 6/1993 | Gubin et al. |
| 5,284,867 A | 2/1994 | Kloog |
| 5,324,737 A | 6/1994 | D'Ambra et al. |
| 5,434,295 A | 7/1995 | Mechoulam et al. |
| 5,440,052 A | 8/1995 | Makriyannis et al. |
| 5,462,960 A | 10/1995 | Barth et al. |
| 5,489,580 A | 2/1996 | Makriyannis et al. |
| 5,521,215 A | 5/1996 | Mechoulam |
| 5,532,237 A | 7/1996 | Gallant et al. |
| 5,538,993 A | 7/1996 | Mechoulam |
| 5,576,436 A | 11/1996 | McCabe et al. |
| 5,605,906 A | 2/1997 | Lau |
| 5,607,933 A | 3/1997 | D'Ambra et al. |
| 5,618,955 A | 4/1997 | Mechoulam et al. |

(Continued)

FOREIGN PATENT DOCUMENTS

EP    0276732    8/1988

(Continued)

OTHER PUBLICATIONS

Khanolkar et al, Head Group Analogs of Arachidonylethanolamide, 1996, J. Med. Chem., vol. 39 No. 22, pp. 4515-4519.*

(Continued)

*Primary Examiner* — Alton N Pryor
(74) *Attorney, Agent, or Firm* — Alix, Yale & Ristas, LLP

(57) ABSTRACT

Analogs that inhibit the transport of anandamide across cell membranes. The inhibitors are amide and ester analogs of anandamide having a tail portion X that is a fatty acid chain remnant, a central portion Y that is an amide or ester radical and a head portion Z that is selected from a variety of groups including hydrogen, alkyl, hydroxy alkyl, aryl, hydroxy aryl, heterocyclic and hydroxy heterocyclic radicals. The disclosed analogs have potential pharmaceutical uses as drugs for treating a variety of diseases and afflictions, including cardiovascular diseases and blood pressure disorders.

10 Claims, 5 Drawing Sheets

U.S. PATENT DOCUMENTS

| | | | |
|---|---|---|---|
| 5,624,941 | A | 4/1997 | Barth et al. |
| 5,631,297 | A | 5/1997 | Pate et al. |
| 5,635,530 | A | 6/1997 | Mechoulam |
| 5,688,825 | A | 11/1997 | Makriyannis et al. |
| 5,744,459 | A | 4/1998 | Makriyannis et al. |
| 5,747,524 | A | 5/1998 | Cullinan et al. |
| 5,804,601 | A | 9/1998 | Kato et al. |
| 5,817,651 | A | 10/1998 | D'Ambra et al. |
| 5,872,148 | A | 2/1999 | Makriyannis et al. |
| 5,874,459 | A * | 2/1999 | Makriyannis et al. ........ 514/425 |
| 5,925,628 | A | 7/1999 | Lee et al. |
| 5,925,768 | A | 7/1999 | Barth et al. |
| 5,932,610 | A | 8/1999 | Shohami et al. |
| 5,939,429 | A | 8/1999 | Kunos et al. |
| 5,948,777 | A | 9/1999 | Bender et al. |
| 6,013,648 | A | 1/2000 | Rinaldi et al. |
| 6,028,084 | A | 2/2000 | Barth et al. |
| 6,096,740 | A | 8/2000 | Mechoulam |
| 6,127,399 | A | 10/2000 | Yuan |
| 6,166,066 | A | 12/2000 | Makriyannis et al. |
| 6,284,788 | B1 | 9/2001 | Mittendorf et al. |
| 6,391,909 | B1 | 5/2002 | Makriyannis et al. |
| 6,579,900 | B2 | 6/2003 | Makriyannis et al. |
| 7,161,016 | B1 * | 1/2007 | Makriyannis et al. .......... 554/67 |
| 2002/0119972 | A1 | 8/2002 | Leftheris et al. |
| 2002/0173528 | A1 | 11/2002 | Fride et al. |
| 2003/0120094 | A1 | 6/2003 | Makriyannis et al. |

FOREIGN PATENT DOCUMENTS

| | | |
|---|---|---|
| EP | 0444451 | 9/1991 |
| EP | 0471609 | 6/1993 |
| EP | 0576357 | 12/1993 |
| EP | 0737671 | 10/1996 |
| EP | 0860168 | 9/2001 |
| FR | 2240003 | 5/1975 |
| FR | 2735774 | 1/2000 |
| GB | 2027021 A | 2/1980 |
| IL | 1995-113228 | 9/1999 |
| JP | 57098228 | 6/1982 |
| JP | 2304080 | 12/1990 |
| WO | WO 94/12466 | 6/1994 |
| WO | WO 97/00860 | 1/1997 |
| WO | WO 97/21682 | 6/1997 |
| WO | WO 97/45407 | 12/1997 |
| WO | WO 99/57106 | 11/1999 |
| WO | WO 99/57107 | 11/1999 |
| WO | WO 00/32200 | 6/2000 |
| WO | WO 01/28329 | 4/2001 |
| WO | WO 01/28497 | 4/2001 |
| WO | WO 01/28498 | 4/2001 |
| WO | WO 01/28557 | 4/2001 |
| WO | WO 01/29007 | 4/2001 |
| WO | WO 01/32169 | 5/2001 |
| WO | WO 01/58869 | 8/2001 |
| WO | WO 02/058636 | 8/2002 |
| WO | WO 02/060447 | 8/2002 |

OTHER PUBLICATIONS

DiMarzo et al, Interactions between synthetic vanilloids and the endogenous cannabinoid system, FEBS Letters 1998, 436(3), 449-54.*

Beltramo et al, Anandamide transprot inhibition by the vanilloid agonist olvanil, European J. of Pharmocology, 1999, 364 (1), 75-8.*

Melck et al, Unsaturated Long-Chain N-Acyl-vanillyl-amides, Biochemical and Biophysical Res. Commun., 1999, 262 (1), 275-284.*

Beltramo et al, Functional role of high-affinity anandamide transport, as revealed by selective inhibition, Science, 277, 1997, 1094-1097.*

Calignano et al, Potentiation of anandamide hypotension by the transport inhibitor, AM404, European J. of Pharmacology, 1997, vol. 337 No. 1, R1-R2 (abs).*

Abadji et al (R-Methanandamide: A Chiral Novel Anandamide Possessing Higher Potency and Metabolic Stability, J. of Medicinal Chem., 1994, vol. 37, No. 12, pp. 1889-1893).*

Calignano et al (Potentiation of anandamide hypotension by the transport inhibitor, AM404, European J. of Pharm, 1997, vol. 337, pp. R1-R2.*

Beltramo et al. (Anandamide transport inhibition by the vanilloid agonist olvanil, European Journal of Pharmacology 364, 1999, 75-78).*

Street et al. (Slow- and Tight-Binding Inhibitors of the 85-kDa Human Phospholipase A2, Biochemistry, 32, 1993, 5935-40).*

Machoulam et al, Identification of an endogenous 2-monoglyceride, present in canine cut, that binds to cannabinoid receptors, Biochemical Pharmacology, vol. 50 (1), pp. 83-90, 1995.*

"Roles of Mu, Delta and Kappa Opioid Receptors in Spinal and Supraspinal Mediation of Gastrointestinal Transit Effects and Hot-Plate Analgesia in the Mouse," F. Porreca, H. I. Mosberg, R. Hurst, V.J. Hruby and T.F. Burks; *J. Pharmacol. Exp. Ther.*, 230: 341-8 (1994).

"Anandamide, an Endogenous Cannabinoid, Inhibits Calcium Currents as a Partial Agonist in N18 Neuroblastoma Cells", K. Mackie, W.A. Devane and B. Hille, *Mol. Pharmacol.*, 44:498-503 (1993).

Abstract from "Anandamide, a brain endogenous compound, interacts specifically with cannabinoid receptors and inhibits adenylate cyclase", Z. Vogel, J. Barg, R. Levy, D. Saya, E. Heldman, R. Mechoulam; *J. Neurochem.*, 61(1):352-5 (1993).

U.S. Appl. No. 10/110,865, filed Oct. 18, 2000, Makriyannis et al.
U.S. Appl. No. 10/110,830, filed Oct. 18, 2000, Makriyannis et al.
U.S. Appl. No. 10/110,812, filed Oct. 18, 2000, Makriyannis et al.
U.S. Appl. No. 10/110,862, filed Oct. 18, 2000, Makriyannis et al.
U.S. Appl. No. 10/111,059, filed Oct. 18, 2000, Makriyannis et al.

Alo, B.I., Kandil, A.; Patil, P. A.; Sharp, M. J.; Siddiqui, M. A.; and Snieckus, V. Sequential Directed Ortho Metalation-Boronic Acid Cross-Coupling Reactions. A general Regiospecific Route to Oxygenerated Dibenzo[b,d]pyran-6-ones Related to Ellagic Acid, J. Org. Chem. 1991, 56, 3763-3768.

*** Archer et al; "cannabinoids, synthesis approaches to 9-ketocannabinoids."; J. Org. Chem.; vol. 42; No. 13; 2277-2284; (1977).

Arnone M., Maruani J., Chaperon P, et al, Selective inhibition of sucrose and ethanol intake by SR141716, an antagonist of central cannabinoid (CB1) receptors, Psychopharmacal, (1997) 132, 104-106. (abstract only).

Beak, P.; and Brown, R A., The Tertiary Amide as an Effective Director of Ortho Lithiation, J. Org. Chem. 1982, 47, 34-36.

Belgaonkar et al; "synthesius of isocoumarins"; Indian J. Chem; vol. 13; No. 4; 336-338; 1975 (abstract only).

Berdyshev EV, Cannabinoid receptors and the regulation of immune response. Chem Phys Lipids. Nov. 2000; 108(1-2):169-90.

Bodnar, V.N., Lozinskii, M.O., Pel'kis, P.S.; "Synthesis of 2,5-disubstituted 1,3,4-oxadiazoles and 1,4-dihydro-1,2,4,5-tetrazines"; Ukrainskii Khimicheskii Zhurnal (Russian Edition); 48(12); 1308-1311; 1982 (abstract only).

Brenneisen R, Pgli A, Elsohly MA, Henn V. Spiess Y: The effect of orally and rectally administered 9-tetrahydrocannabinol on spasticity, a pilot study with 2 patients. Int. J. Clin Pharmacol Ther. (1996) 34:446-452. (abstract only).

***Brotchie JM: Adjuncts to dopamine replacement a pragmatic approach to reducing the problem of dyskinesia in Parkinson's disease. Mov. Disord. (1998)13:871-876.

Brown et al; "Synthesis and hydroboration of (-)-2-phenylapopinene, Comparison of mono(2-phenylapoisopinocampheyl)borane with its 2-methyl and 2-ethyl analogues for the chiral hydroboration of representative alkenes"; J. Org. Chem.; 55(4); 1217-1223; (1990).

Buckley NE, McCoy KI, Mpzey E et al, "Immunomodulation by cannabinoids is absent in mice deficient for the cannabinoid CB2 receptor"; Eur. J Pharmacol (2000) 396:141-149.

Burstein et al; "detection of cannabinoid receptors . . . "; Biochem. Biophys. Res. Commun.; vol. 176(1); 492-497; 1991 (abstract only).

Busch-Peterson et al; "Unsaturated side chain beta-11-hydroxyhexahydrocannabinol analogs"; J. Med. Chem.; 39; 3790-3796; (1996).

Calignano A, La Rana G. Diuffrida A, Piomelli D; "Control of pain initiation by endogenous cannabinoids"; Nature (1998) 394:277-291. (abstract only).

Campbell FA et al; "Are cannabinoids an effective and safe treatment option in the management of pain? A qualitative systematic review"; BMJ. Jul. 7, 2001;323(7303):13-6.

Charalambous A. et al; "5'-azido 8-THC: A Novel Photoaffinity Label for the Cannabinoid Receptor"; J. Med. Chem., 35, 3076-3079 (1992).

Charalambous A. et al; "Pharmacological evaluation of halogenated . . . "; Pharmacol. Biochem. Behav.; vol. 40; No. 3; 509-512; 1991.

Cheng et al; "Relationship Between the Inhibition Constant (Ki) and the concentration of Inhibitor which causes 50% Inhibition (IC50) of an Enzymatic Reaction"; Biochem. Pharmacol., 22, 3099-3102, (1973) (abstract only).

Colombo G, Agabio R, Diaz G. et al; "Appetite suppression and weight loss after the cannabinoid antagonist SR141716"; Life Sci. (1998) 63-PL13-PL117. (abstract only).

Compton et al; "Synthesis and pharmacological evaluation of ether and related analogues of delta8-. delta9- and delta9,11-tetrahydrocannabinol"; J. Med. Chem; vol. 34; No. 11; 3310-3316; 1991.

Consroe P, Musty R, Rein J, Tillery W, Pertwee R; "The perceived effects of smoked cannabis on patents with multiple sclerosis"; Eur. Neurol. (1997) 38-44-48. (abstract only).

Coxon et al; "Derivatives of nopinone"; Aust. J. Chem.; 23; 1069-1071; (1970) (abstract only).

Crawley et al; "Anandamide, an endogenous ligand of the cannabinoid receptor, induces hypomotility and hypothermia in vivo in rodents"; Pharmacology Biochemistry and Behavior; vol. 46; 967-972; 1993.

D'Ambra et al; "C-attached aminoalkylindoles: potent cannabinoid mimetics"; Bioorg. & Med. Chem. Lett., 1996, 6(1), 17-22.

DePetrocellis L, Melck D, Palmisano A. et al; "The endogenous cannabinoid anandamide inhibits human breast cancer cell proliferation"; Proc. Natl. Acad. Sci. USA (Jul. 1998) 95:8375-8380.

Devane, W.A. et al; "Determination and Characterization of a Cannabinoid Receptor in a Rat Brain"; Mol. Pharmacol., 34, 605-613 (1988). (abstract only).

Di Marzo, V., Melck, D., Bisogno, T., DePetrocellis, L.; "Endocannabinoids: endogenous cannabinoid receptor ligands with neuromodulatory action"; Trends Neurosci. (1998) 21:521-528.

*** Dodd, P.R. et al, A Rapid Method for Preparing Synaptosomes: Comparison with Alternative Procedures, *Brain Res.*, 226, 107-118 (1981).

Dominiami et al; "Synthesis of 5-(tert-Alkyl)resorcinols"; J. Org. Chem. 42(2); 344-346; (1977).

Drake et al, "classical/nonclassical hybrid cannabinoids"; J. Med. Chem.; vol. 41(19); 3596-3608 (1998).

Edery et al; "Activity of novel aminocannabinoids in baboons"; J. Med. Chem.; 27; 1370-1373 (1984).

Eissenstat et al; "Aminoalkylindoles: structure-activity relationships of novel cannabinoid mimetics"; J. Med. Chem. 1995, vol. 38, No. 16, pp. 3094-3105; XP 000651090.

Fahrenholtz, K. E., Lurie, M. and Kierstead, AR. W.; "The Total Synthesis of dl-Δ9-Tetrahydrocannabinol and Four of Its Isomers"; J. Amer. Chem. Soc. 1967, 89(23), 5934-5941.

Fahrenholtz; "The synthesis of 2 metabolites of (-)-delta eight-tetrahydrocannabinol"; J. Org. Chem.; vol. 37(13); 1972; XP002111824.

Fisera, L., Kovac, J., Lesco, J., Smahovsky, V.; "Furan derivatives. Part CLVI. 1,3-dipolar cycloadditions of heterocycles. V. Reaction of C-acetyl-N-phenylnitrilimine with furan derivatives"; Chemicke Zvesti; 35(1); 93-104 1981 (abstract only).

Galiegue S et al. ; "Expression of central and peripheral cannabinoid receptors in human immune tissues and leukocyte subpopulations"; Eur J Biochem.; Aug. 15, 1995;232(1):54-61. (abstract only).

Gareau, Y.; Dufresne, C.; Gallant, M.; Rochette, C.; Sawyer, N.; Slipetz, D.M.; Tremblay, N.; Weech, P. K.; Metters, K. M.; Labelle, M.; "Structure activity relationships of tetrahydrocanabinol analogs on human cannabinoid receptors"; Bioorg. Med. Chem. Lett. 1996, 6(2), 189-194.

Gold et al; "A comparison of the discriminative stimulus properties of delta9-tetrahydrocannabinol and CP 55,940 in rats and rhesus monkeys"; J. Pharmacol. Exp. Ther.; vol. 262(2); 479-486; 1992.

*** Green K. Marijuana smoking vs. cannabinoids for glaucoma therapy. *Arch. Ophibalmol.* (1998) feb 433-1437.

Hampson, A.J., Grimaldi M. Axpirod J. Wink D; "Cannabidiol and (-) 9 tetrahydrocannabinol are neuroprotective antioxidants"; Proc. Natl Acad Sci. USA (Jul. 1998) 95; 8268-8273.

Hargreaves, K. et al; "A new sensitive method for measuring thermal nociception in cutaneous hyperalgesia"; Pain; 32; 77-88; (1988) (abstract only).

*** Hemming M, Yellowlees PM; "Effective treatment of Tourette's syndrome with marijuana"; *J. Psychopharmacol*, (1993) 7:389-391.

Herzberg U, Eliav E, Bennett GJ, Kopin IJ; "The analgesic effects of R(+) WIN 55,212-2 mesylate, a high affinity cannabinoid agonist in a rat model of neuropathic pain" ; Neurosci. Letts. (1997) 221; 157-160.

*1* Horrevoets A.J.G et al; "Inactivation of reconstituted *Escherichia coli* outer membrane phospholipase A by membrane-perturbing peptides results in an increased reactivity towards the affinity label hexadecanesulfonyl fluoride"; Eur. J. Biochem.; 198; 255-261; 1991.

Howlett et al; "Azido and isothicyanato substituted aryl pyrazoles bind covalently to the CB1 cannabinoid receptor and impair signal transduction"; Journal of Neurochemistry; vol. 74(5) (2000) 2174-2181; XP001097394.

Howlett et al; "Stereochemical effects of 11-OH-delta 8 tetrahydrocannabinol-dimethylheptyl to inhibit adenylate cyclase and bind to the cannabinoid receptor"; Neuropharmacology; vol. 29(2); 161-165; 1990.

Huffman et al; "3-(1',1'-dimethylbuty1)—deoxy-delta 8THC and related compounds: synthesis of selective ligands for the CB2 receptor"; Bioorganic and Medicinal Chemistry; vol. 7; 2905-2914; (1999).

Huffman et al; "Stereoselective synthesis of the epimeric delta 7-tetrahydocannabinols"; tetrahedron; vol. 51(4); 1017-1032; (1995).

Huffman et al; "Synthesis of 5',11 dihydroxy delta 8 tetrahydrocannabinol"; Tetrahedron, vol. 53(39), pp. 13295-13306 (1997).

Huffman et al; "Synthesis of a tetracyclic, conformationally constrained analogue of delta8-THC"; Bioorganic & Medicinal Chemistry; vol. 6(12); 2281-2288; 1998; XP002123230.

Huffman et al; "Synthesis of both enantiomers of Nabilone from a common intermediate. Enantiodivergent synthesis of cannabinoids"; J. Org. Chem.; 1991, 56, 2081-2086.

*** Joy JE, Wagtson SJ, Benson JA; "Marijuana and Medicine Assessing the Science Base"; *National Academy Press*, Washington, DC, USA (1999).

Kaminski NE; "Regulation of the cAMP cascade, gene expression and immune function by cannabinoid receptors"; J Neuroimmunol. Mar. 15, 1998;83(1-2):124-32.

Khanolkar et al; "Molecular probes for the cannabinoid receptors"; Chemistry and Physics of Lipids; 108; 37-52; (2000).

Klein T.W. et al, "The cannabinoid system and cytokine network"; Proc Soc Exp Biol Med. Oct. 2000; 225(1):1-8; (abstract only).

Klein TW et al, "Cannabinoid receptors and immunity"; Immunol Today; Aug. 1998; 19(8):373-81.

Kumar RN, et al; "Pharmacological actions and therapeutic uses of cannabis and cannabinoids"; Anesthesia, 2001, 56: 1059-1068 (abstract only).

Lan, R et al; "Structure activity relationships of pyrazole derivatives as cannabinoid receptor antagonists"; J. Med. Chem.; vol. 42(4); 769-776; (1999).

Lavalle et al; "Efficient conversion of (1R, 5R)-(+)-alpha-pinene to (1S, 5R)-(−)-nopinene"; J. Org. Chem.; vol. 51(8); 1362-1365; (1986).

Loev, B., Bender, P. E., Dowalo, F., Macko, E., and Fowler, P.; "Cannabinoids. Structure-Activity Studies Related to 1,2-Dimethylheptyl Derivatives"; J. Med. Chem.; vol. 16(11); 1200-1206; 1973.

Lozinskii, M.O., Bodnar, V.N., Konovalikhin, S.V., D'yachenko, O.A., Atovmyan, L.O.; "Unusual transformations of arylhydrazonoyl chlorides of oxalic acid ethyl ester"; Izvestiya Akademii Nauk SSSr, Seriya Khimicheskaya; 11; 2635-2637; 1990 (abstract only).

Ludt, R.E. et al; "A comparison of the synthetic utility of n-butyllithium and lithium diisopropylamide in the metalations of N,N-dialkyltouamides"; J. Org. Chem.; 38(9); 1668-1674 (1973).

\*\*\* Maccarron M., Endocannabinoids and their actions. *Vitamins and Hormones* 2002;65:225-255.

\*\*\* Markwell et al; *Anal. Biochem.*; 87:206 (1978).

Martin et al; "Behavioral, biochemical, and molecular modeling evaluations of cannabinoid analogs"; Pharmacol. Biochem. Behav.; vol. 40(3); 471-478; 1991.

Martyn CN. Illis LS, Thom J.; "Nabilone in the treatment of multiple sclerosis"; Lancet (1995) vol. 345; pp. 579.

Matsumoto et al; "Cannabinoids 1.1-amino-and 1 mercapto-7,8,9,10-tetrahydro-6h-dibenzo[b,d]pyrans"; J. of Med. Chem.; vol. 20(1); 17-24; 1977; XP00211825.

\*\*\* Maurer M, Henn V, Dittrich A, Hofmann A. Delta-9-tetrahydrocannabinol shows antispastic and analgesic effects in a single case double-blind trial. *Eur. Arch. Psychiat. Clin.* Neurosci. (1990); Z40:1-4.

Mavromoustakos, T. et al; "Studies on the thermotropic effects of cannabinoids on phosphatidylcholine bilayers using differential scanning calorimetry and small angle X-ray diffraction"; Biochimica et Biophysica Acta; vol. 1281(2); 1996; XP002111823.

Mechoulam et al; "Stereochemical Requirements for cannabinoid activity"; J. Med. Chem.; 23(10); 1068-1072; (1980).

Mechoulam et al; "Synthesis of the individual, pharmacologically distinct, enantiomers of a tetrahydrocannabinol derivative"; Tetrahedron Asymmetry; 1: 311-314; (1990) (abstract only).

\*\*\* Mechoulam et al; *Tetrahedron Asymmetry*; 1: 315-318; (1990).

\*\*\* Mechoulam, "Cannabinoids as therapeutic agents"; *CRC press*, 1986.

Meltzer et al; "An improved synthesis of cannabinol and cannabiorcol"; Synthesis; 1981:985 (1981).

\*\*\* Melvin et al; drug design and discovery; 13; 155-166 (1995).

Melvin et al; "Structure-activity relationships for cannabinoid receptor-binding and analgesic activity: studies of bicyclic cannabinoid analogs"; Mol. Pharmacol.; 44(5); 1008-1015 (1993).

Merck Index; 11th edition; "Tetrahydrocannabinols" compound No. 9142; 1989.

\*\*\* Morgan Dr: Therapeutic Uses of Cannabis. *Harwood Academic Publishers*, Amsterdam. (1997).

\*\*\* Morris, S,; Mechoulam, R.; and Irene, Y., Halogenation of phenols and Phenyl ethers with Potassium Halides in the Presence of 18-Crown-6 on Oxidation with m-Chloroperbenzoic Acid, *J. Chem. Soc.*, Perkin Trans. 1 1987, 1423-1427.

\*\*\* Muller-Vahl KB, Kolbe H, Schneider U, Emrich, HM Cannabis in movement disorders. Porsch. Kompicmentarmed (1999) 6 (suppl. 3) 23-27.

\*\*\*Muller-Vahl KB, Schneider U, Kolbe H, Emrich, HM. Treatment of Tourette's syndrome with delta-9-tetrahydrocannabinol. *Am. J.* Psychiat. (1999) 156-195.

Novak, J et al; Cannabis, part 27, synthesis of 8-, 10- and 11-oxygenated cannabinoids; J. Chem. Soc. Perkin Trans.; 2867-2871; (1983) (abstract only).

Nye et al; "High affinity cannabinoid binding sites in brain membranes labelled with [H]-5'-trimethylammonium delta8-tetrahydrocannabinol"; J. Pharmacol. Exp. Ther.; vol. 234(3); 784-791; 1985.

\*\*\* Palmer et al; current pharmaceutical design; 6; 1381-1397; (2000).

Papahatjis et al; "A new ring-forming methodology for the synthesis of conformationally constrained bioactive molecules"; Chemistry Letters, 192; (2001).

Papahatjis et al; "Pharmacophoric requirements for cannabinoid side chains: multiple bond and C1'-substituted delta8-tetrahydrocannabinols"; J. Med. Chem.; 41(7); 1195-1200; (1998).

Pertwee et al; "AM630, a competitive cannabinoid receptor agonist"; Life Sci. 1995, 56(23/24), 1949-1955; XP 000653566.

Pertwee et al; "Pharmacological characterization of three novel cannabinoid receptor agonists in the mouse isolated vas deferens"; Eur. J. Pharmacol. 1995, 284, 241-247; XP-001041044.

Pertwee; Pharmacology of cannabinoid CB1 and CB2 receptors; Pharmacol. Ther., vol. 74(2); pp. 129-180; (1997); XP002226467.

Petrov, M.L., Terent'eva, N. A., Potekhin, K.A., Struchkov, Yu. T.; ".alpha.,.beta.-unsaturated thiolates and their analogs in cycloaddition reactions. XVIII. Reaction of (2-phenylethynyl)tellurolates with C-ethoxycarbonyl-N-Phenylnitrilimine"; Zhurnal Organicheskoi Khimii; 29(7); 1372-1378; (1993) (abstract only).

\*\*\* Pinnegan-Ling D, Musty R.; Marinol and phantom limb pain: a case study. *Proc Inv. Cannabinoid Rea. Sec.* (1994):53.

Pitt et al; "The synthesis of Deuterium, carbon-14 and carrier free tritium labelled cannabinoids"; Journal of Labellled Compounds; vol. 11(4); 551-575; 1975; XP002123229.

Razdan et al; "Drugs delivered from cannabinoids. 6. .Synthesis of cyclic analogues of dimethylheptylpyran"; J. Med. Chem.; vol. 19(5); 719-721; 1976 (abstract only).

Reggio et al; "Characterization of a region of steric interference at the cannabinoid receptor using the active analog approach"; J. Med. Chem. United States; vol. 36(12); 1761-1771; 1993.

Rhee, M. H.; Vogel, Z.; Barg, J.; Bayewitch, M.; Levy, R.; Hanus, L.; Breuer, A.; and Mechoulam, R.; "Cannabinol Derivatives: Binding to Cannabinoid Receptors and Inhibition of Adenylcyclase"; J. Med. Chem. 1997, 40(20); 3228-3233.

\*\*\* Rice AS. Cannabinoids and pain. *Curr Opin Investig Drugs*. Mar. 2001;2(3):399-414.

Richardson JD, Aanonsen I, Hargreaves KM; "Antihyperalgesic effects of spinal cannabinoids"; Eur. J. Pharmacol. (1998) 346:145-153.

Richardson JD, Kilo S. Hargreaves KM; "Cannabinoids reduce hyperalgesia and inflammation via interaction with peripheral CB1 receptors"; Pain (1998) 75:111-119.

Rinaldi-Carmona et al; "Biochemical and pharmacological characterization of SR141716A, the first potent and selective brain cannabinoid receptor antagonist"; Life Sci.; vol. 56(23/24); 1941-1947 (1995).

Rinaldi-Carmona et al; "SR141716A, a potent and selective antagonist of the brain cannabinoid receptor"; FEBS Lett.; 350; 240-244; (1994).

Rompp Chemie Lexikon; Falbe and Regitz; "band 1-A-C1, 8"; Aufl, Thieme Verlag; Stuttgart, S 569-570; 1989.

Santus, Maria; "Studies on thioamides and their derivatives. IX. Synthesis of the derivatives of 1,2,4,5-tetrazine"; Acta Polonae Pharmaceutica; 50(2-3); 183-188; 1993 (abstract only).

Schatz AR et al; "Cannabinoid receptors CB1 and CB2: a characterization of expression and adenylate cyclase modulation within the immune system"; Toxicol Appl Pharmacol. Feb. 1997; 142(2):278-87.

\*\*\* Schuel, H., Burkman, L.J., Picone, R.P., Bo, T., Makriyannis, A., Cannabinoid receptors in human sperm. *Mol. Biol. Cell.*, (1997) (8), 325a.

Shawali, A.S., Albar, H.A.; "Kinetics and mechanism of dehydrochlorination Of N-aryl-C-ethoxycarbonyl formohydrazidoyl chlorides"; Canadian Journal Of Chemistry; 64(5); 871-875; 1986 (abstract only).

\*\*\* Shen M. Thayer SA: Cannabinoid receptor agonists protect cultured rat hippocampal neurons from excitotoxicity. *Mol. Pharmacol* (1996) 54:459-462.

Shim et al; "Three-dimensional quantitative structure-activity relationship study of the cannabimimetic (aminoalkyl)indoles using comparative molecular field analysis"; J. Med. Chem.; 1998, 41(23); 4521-4532; XP-002212407.

Shim et al; "Unified pharmacophoric model for cannabinoids and aminoalkylindoles derived from molecular superimposition of CB1 cannabinoid receptor agonists CP55244 and WIN55212-2"; ACS Symposium series, 1999 719 (rational drug design), 165-184; XP-001095771.

Showalter et al; "Evaluation of binding in a transfected cell line expressing a peripheral cannabinoid receptor (CB2): identification of cannabinoid receptor subtype selective ligands"; J. Pharmacol. Exp. Ther., 1996 278(3) 989-999; XP-001097918.

\*\*\* Simiand J, Keane M, Keane PE, Soubrie P: SR 141716, A CB1 cannabinoid receptor antagonist, selectively reduces sweet food intake in marmoset. *Behav. Pharmacol* (1998) 9:179-181.

\*\*\* Terranova J-P, Storme J-J Lafon N. et al; "Improvement of memory in rodents by the selective CB1 cannabinoid receptor antagonist, SR 141716"; *Psycho-pharmacol* (1996) 126:165-172.

Tius et al; "Conformationally restricted hybrids of CP-55,940 and HHC: Steroeselective synthesis and activity"; Tetrahedron; 50 (9); 2671-2680; (1994) (abstract only).

\*\*\* Ueda, N., Endocannabinoid hydrolases. *Prostaglandins & Other Lipid* Mediators 2002;68-69:521-534.

\*\*\* Wagner JA, Varga K, Jarai Z, Kunos G; 'Mesenteric vasodialtion mediated by endothelia anandamide receptors'; *Hypertension* (1999) 33:429-434.

Watanabe, T.; Miyaura, N.; and Suzuki, A.; "Synthesis of Sterically Hindered Biaryls via the Palladium Catalyzed Cross-Coupling Reaction of Arylboronic Acids or their Esters with Haloarenes"; Synlett 1992, 207-210.

Wiley et al; "Structure activity relationships of indole and pyrrole derived cannabinoids"; J. Pharmacol. Exp. Ther. 1998, 285(3), 995-1004; XP-001097982.

Wilson et al; "9-nor-delta8-tetrahydrocannabinol, a cannabinoid of metabolic intersts"; J. Med. Chem.; 17(4); 475-476; (1974).

Wilson et al; "Analgesic properties of the tetrahydrocannabinols, their metabolites and analogs"; J. Med. Chem.; 18(7); 700-703; (1975).

Wilson et al; "9-nor-9-hydrohexahydrocannabinols. Synthesis, some behavioral and analgesic properties, and comparison with the tetrahydrocannabinols"; J. Med. Chem.; 19(9); 1165-1167; (1976).

Yamada et al; "(Aminoalkyl)indole isothiocyanates as potentiual electrophilic affinity ligands for the brain cannabinoid receptor"; J. Med. Chem. 1996, vol. 39(10), 1967-1974.

Yan, Guo et al; "Synthesis and pharmacological properties of 11-hydroxy-3-(1'-1'-dimethylheptyl)hexahydrocannabinol: a high affinity cannabinoid agonist"; J. Med. Chem.; vol. 37(16); 2619-2622; (1994).

Yan Guo et al; "(-)-11-hydroxy-7'-isothiocyanato-1'-1'dimethylheptyl-delta8-THC: a novel probe for the cannabinoid receptor in the brain"; J. Med. Chem.; 37(23); 3867-3870; (1994).

U.S. Appl. No. 09/698,071, filed Oct. 30, 2000, Fride et al.

\*2\* Brotchie JM: Adjuncts to dopamine replacement a pragmatic approach to reducing the problem of dyskinesia in Parkinson's disease. Mov. Disord. (1998)13:871-876. (abstract only).

Compton D.R. et al; "Pharmacological Profile Of A Series of Bicyclic Cannabinoid Analogs: Classification as Cannabimimetic Agents"; J. Pharmacol. Exp. Ther.; 260; 201-209; 1992. (abstract only).

\*2\* Dodd, P.R. et al, A Rapid Method for Preparing Synaptosomes: Comparison with Alternative Procedures, Brain Res., 226, 107-118 (1981). (abstract only).

\*2\* Green K.; "Marijuana smoking vs. cannabinoids for glaucoma therapy."; Arch. Ophthalmol. (1998) Nov. 116(11); 1433-1437. (abstract only).

Griffin, G., Wray, E. J., Tao, Q., McAllister, S. D., Rorrer, W. K., Aung, M., Martin, B. R., Abood, M. E.; "Evaluation of the cannabinoid CB2 receptor selective antagonist, SR144528: further evidence for cannabinoid CB2 receptor absence in the rat central nervous system"; European Journal of Pharmacology; (1999); vol. 377; 117-125.

\*1\* Hanus et al; "Two new unsaturated fatty acid ethanolamides in brain that bind to the cannabinoid receptor"; Journal of medicinal Chemistry; 36(20); 3032-3034; 1993.

Jbilo, O., Derocq, J., Segui, M., Le Fur, G., Casellas, P.; "Stimulation of peripheral cannabinoid receptor CB2 induces MCP-1 and IL-8 gene expression in human promyelocytic cell line HL60"; FEBS Letters; (1999); vol. 448; No. 21848; 273-277.

\*2\* Joy JE, Watson SJ, Benson JA; "Marijuana and Medicine Assessing the Science Base"; National Academy Press, Washington, DC, USA (1999). (abstract only).

\*1\* Lang, W. et al; "Substrate Specificity and Stereoselectivity of Rat Brain Microsomal Anandamide Amidohydrolase"; J. Med. Chem.; vol. 42(5); 896-902; (1999).

\*1\* Lang, W., Qin, C., Hill, W.A., Lin, S., Khanolkar, A.D., Makriyannis, A.; High-Performance Liquid Chromatographic Determination Of Anandamide Amidase Activity in Rat Brain Microsomes; Anal. Biochem.; (1996), 238, 40-45 (abstract only).

\*2\* Maurer M, Henn V, Dittrich A, Hofmann A.; "Delta-9-tetrahydrocannabinol shows antispastic and analgesic effects in a single case double-blind trial."; Eur. Arch. Psychiat. Clin. Neurosci. (1990), 240:1-4. (abstract only) .

\*1\* Mechoulam et al; Structural Requirements for Binding of Anandamide Type Compounds to the Brain Cannabinoid Receptor; J. Med. Chem.; 1997; 40; 659-667.

\*1\* Mechoulam et al; "Towards Cannabinoid drugs—Revisited"; Progress in Medicinal Chemistry; 35; 199-243; Jul. 3, 1998.

Meschler, J. P., Kraichely, D. M., Wilken, G. H., Howlett, A. C.; "Inverse Agonist Properties of N-(Piperidin-1-y1)-5-(4-chlorophenyl)-1-(2,4- dichlorophenyl)-4-methyl-1H-pyrazole-3-carboxamide HCL (SR141716A) and 1-(2-Chlorophenyl)-4-cyano-5-(4-methoxyphenyl)-1H-pyrazole-3-carboxylic Acid Phenylamide (CP-272871) for the CB1 Cannabinoid Receptor"; Biochemical Pharmacology; (2000); vol. 60; No. 9; 1315-1322.

Melvin et al; "Structure-Activity Relationships Defining the ACD-Tricyclic Cannabinoids Cannabinoid Receptor Binding and Analgesic Activity"; Drug Design and Discovery; 13(2); 155-166 (1995). (abstract only).

\*2\* Muller-Vahl KB, Kolbe H, Schneider U, Emrich, HM Cannabis in movement disorders. Porsch. Kompicmentarmed (1999) 6 (suppl. 3) 23-27. (abstract only).

\*2\* Muller-Vahl KB, Schneider U, Kolbe H, Emrich, HM.; "Treatment of Tourette's syndrome with delta-9-tetrahydrocannabinol." Am. J. Psychiat.; (1999); 156(3); 495.

Pacheco M, et al; "Aminoalkylindoles: Actions on Specific G-Protein-Linked Receptors"; J. Pharmacol. Exp. Ther.; vol. 257, No. 1, pp. 170-183 and 172 Table (1991).

\*1\* \*2\* Palmer et al; "Natural and Synthetic Endocannabinoids and Their Structure-Activity Relationships"; Current Pharmaceutical Design; 6; 1381-1397; (2000).

\*1\* Pertwee et al; "Inhibitory effects of certain enantiomeric cannabinoids in the mouse vas deferens and the myenteric plexus preparation of guinea-pig small intestine"; Br. J. Pharmacol.; 105(4); 980-984 (1992). (abstract only).

\*1\* Pinto et al; Cannabinoid Receptor Binding and Agonist Activity of Amides and Esters of Arachidonic Acid; Mol. Pharmacol.; 1994; 46(3); 516-522. (abstract only).

\*1\* \*2\*Porretta F., Mosberg H.I., Hurst R., Hruby V.J., Burks T.F.; "Roles of mu, delta and kappa opiod receptors in spinal and supraspinal mediation of gastrointestinal transit effects and hot-plate analgesia in the mouse"; J. Pharmacol. Exp. Ther.; 230(2); 341-348; (1994). (abstract only).

Quere, L., Boigegrain, R., Jeanjean, F., Gully, D., Evrard, G., Durant, F.; "Structural requirements of non-peptide neurotensin receptor antagonists"; J. Chem Soc., Perkin Trans. 2, (1996); 2639-2646.

\*1\* Razdan et al; "Pharmacological and Behavioral Evaluation of Alkylated Anandamide Analogs"; Life Sci.; 1995; 56(23-24); 2041-2048 (abstract only).

\*2\* Rice AS. Cannabinoids and pain. Curr Opin Investig Drugs. Mar. 2001;2(3):399-414. (abstract only).

\*1\* \*2\* Serdarevich B., Caroll K.K., "Synthesis and characterization of 1- and 2-monoglycerides of anteiso fatty acids"; J. Lipid Res.; 7; 277-284; (1966).

\*2\* Shen M. Thayer SA: Cannabinoid receptor agonists protect cultured rat hippocampal neurons from excitotoxicity. Mol. Pharmacol (1996) 54:459-462.

\*1\* Sheskin, T. et al; Structural Requirements for Binding of Anandamide Type Compounds to the Brain Cannabinoid Receptor; J. Med. Chem.; 1997; 40; 659-667.

\*2\* Simiand J, Keane M, Keane PE, Soubrie P: SR 141716, A CB1 cannabinoid receptor antagonist, selectively reduces sweet food intake in marmoset. Behav. Pharmacol (1998) 9:179-181. (abstract only).

\*2\* Terranova J-P, Storme J-J Lafon N. et al; "Improvement of memory in rodents by the selective CB1 cannabinoid receptor antagonist, SR 141716"; Psycho-pharmacol (1996) 126:165-172 (abstract only).

Tetko, I. V. et al; "Volume Learning Algoritm Artificial Neural Networks for 3D QSAR Studies"; J. Med. Chem.; vol. 44, No. 15 (2001) pp. 2411-2420, 2413, 2414 Table 1.

\*2\* Ueda, N., Endocannabinoid hydrolases. Prostaglandins & Other Lipid Mediators 2002;68-69:521-534 (abstract only).

\*2\* Vogel Z., Barg J., Levy R., Saya D., Heldman E., Mechoulam R.; "Anandamide, a brain endogenous compound, interacts specifically with cannabinoid receptors and inhibits adenylate cyclase"; J. Neurochem.; 61(1) 352-355; (1993) (abstract only).

*2* Wagner JA, Varga K, Jarai Z, Kunos G; "Mesenteric Vasodilation Mediated by Endothelia Anandamide Receptors"; Hypertension (1999) 33:429-434.

Berglund et al; "Structural requirements for arachidonylethanolamide interaction with CB1 and CB2 cannabinoid receptors: . . ."; Prostanglandins, leukotrienes ands essential fatty acids; 59(2); 111-118; (1998). (abstract only).

*** BioWorld Today, vol. 8(162), Aug. 21, 1997.

Cherest M., Luscindi X.; "The action of acetyl chloride and of acetic anhydride on the lithium nitronate salt of 2-phenylnitroethane . . ."; Tetrahedron; 42(14); 3825-3840; 1986; in French with English abstract.

Cherest M., Lusinchi X.; "A novel electrophilic N-amidation via electron deficient complexes: action of ferric chloiride on N-acetyloxyamides"; Tetrahedron Letters; 30(6); 715-718; 1989.

*** Compton D.R. et al; J. Pharmacol. Exp. Ther.; 260; 201-209; 1992.

*** D'Amour F.E., Smith D.L.; J. Pharmacol. Exp. Ther.; 72, 74-79, 1941.

Demuynck L. et al; "Rearrangement of Indolo[2,3-a]quinolizidines to derivatives with E-azaaspidospermane skeleton"; Tetrahedron Letters; 30(6) 710-722; 1989; in French with English abstract.

Deutsch D.G. et al; "Fatty acid sulfonyl fluorides inhibit anandamide metabolism and bind to cannabinoid receptor"; Biochem. Biophys. Res. Commun. 231(1); 217-221; 1997; CODEN: BBRCA9; ISSN:0006-291X; XP002040933.

Deutsch D.G., Chin S.A.; "Enzymatic synthesis and degradation of anandamide, a cannabinoid receptor agonist"; Biochemical Pharmacology; 46(5); 791-796; 1993.

Fride & Mechoulam; "Pharmacological activity of the cannabinoid receptor agonist; . . ."; European Journal of Pharmacology, vol. 231; 313-314; 1993.

Hillard C. J., Edgemond, W. S., Jarrahian W., Campbell, W. B; "Accumulation of N-Arachidonoylethanolamine (Anandamide) into Cerebellar Granule Cells Occurs via Facilitated Diffusion"; Journal of Neurochemistry; 69; 631-638 (1997).

Horrevoets A.J.G et al; "Inactivation of *Escherichia coli* outer membrane phospholipase A by the affinity label hexadecanesulfonyl fluoride"; Eur. J. Biochem.; 198; 247-253; 1991.

Kawase M. et al; "Electrophilic aromatic substitution with N-methoxy-N-acylnitrenium ions generated from N-chloro-N-methoxyamides: synthesis of nitrogen heterocyclic compounds bearing a N-methoxyamide group"; J. Org. Chem.; 54; 3394-3403; 1989.

Koutek B. et al; "Inhibitors of arachidonyl ethanolamide hydrolysis"; J. Biol. Chem.; 269(37); 22937-40; 1994; CODEN: JBCHA3; ISSN: 0021-9258; XP002040931.

Neunhoeffer O., Gottschlich R.; "Acylating activity of O-acylated hydroxylamine derivatives"; Justus Liebigs Ann. Chem.; 736; 100-109; 1970; in German with English abstract.

*** Pertwee et al; Br. J. Pharmacol.; 105; 980 1992.

Smith P.B. et al; "The Pharmacological activity of anandamide, a putative endogenous cannabinoid, . . ."journal of pharmacology and experimental therapeutics; vol. 270(1):219-227; 1994 (abstract only, attached to Twitchell abstract).

Twitchell, W. et al; "Cannabinoids inhibit N- and P/Q type calcium channels in cultured rat hippocampal neurons"; Journal of Neurophysiology; 78(-1); 43-50; 1997 (database CAPLUS on STN (Columbus, OH, USA) DN 127:199945 (abstract only).

Barnett-Norris et al; "exploration of biologically relevant conformations of anandamide, . . ."; J. Med. Chem.; vol. 41; 4861-4872; 1998.

U.S. Appl. No. 09/701,989, filed Jan. 2001, Makriyannis et al.

"Structural determinants for recognition and translocation by the anandamide transporter", D. Piomelli, M. Beltramo, S Glasnapp, S.Y. Lin, A. Goutopoulos, Xiang-Qun Xie and A. Makriyannis; *Proc. Natl. Acad. Sci. USA*, 96, 5802-5807 (1999).

"Potentiation of anandamide hypotension by the transport inhibitor, AM404", A. Calignano, G. La Rana, M. Beltramo, A. Makriyannis, D. Piomello; *European Journal of Pharmacology*, 337 (1997) R1-R2.

"Inhibition of intestinal motility by anandamide, an endogenous cannabinoid", A. Calignano, G. La Rana, A. Makriyannis, S.Y. Lin, M. Beltramo, D. Piomelli; *European Journal of Pharmacology*, 340 (1997) R7-R8.

"Novel Analogues of Arachidonylethanolamide (Anandamide): Affinities for the CB1 and CB2 Cannabinoid Receptors and Metabolic Stability", S. Lin, A.D. Khanolkar. P. Fan, A. Goutopoulos, C. Qin, D. Papahadjis and A. Makriyannis; *J. Med. Chem.*, 1997.

"Functional Role of High-Affinity Anandamide Transport, as Revealed by Selective Inhibition", *Science*, 277, 1094-1097, (1997).

"(R)-Methanandamide: A Chiral Novel Anandamide Possessing Higher Potency and Metabolic Stability", V. Abadji, S. Lin, G. Taha, G. Griffin, L.A. Stevenson, R.G. Pertwee and A. Makriyannis; *J. Med. Chem.*, 37:1889-93 (1994).

"Synthesis and characterization of 1- and 2-monoglycerides of anteiso fatty acids" B. Serdarevich and K.K. Carroll, *J. Lipid Res.*, 7:277-284 (1966).

"Anandamide Amidohydrolase Activity in Rat Brain Microsomes," F. Desarnaud, H. Cadas and D. Piomelli; *J. Biol. Chem.*, 270:6030-35 (1995).

U.S. Appl. No. 09/250,698, filed Feb. 16, 1999, Makriyannin et al.

* cited by examiner

INHIBITORS OF THE ANANDAMIDE TRANSPORTER

RELATED APPLICATION

This application is based on and claims the benefit under 35 U.S.C. §119(e) of U.S. Provisional Application No. 60/088,568 filed Jun. 9, 1998.

GOVERNMENT FUNDING

This invention was made with Government support under Contract No. DA 3801 awarded by the National Institute of Drug Abuse. The Government has certain rights in the invention.

BACKGROUND OF THE INVENTION

The marijuana derived cannabinoid $\Delta^9$-tetrahydrocannabinol, $\Delta^9$THC, is known to bind to CB1 receptors in the brain and CB2 receptors in the spleen. Compounds which stimulate those receptors have been shown to induce analgesia and sedation, to cause mood elevation including euphoria and dream states, to control nausea and appetite and to lower intraocular pressure. Cannabinoids have also been shown to suppress the immune system. Thus, compounds which stimulate the receptors, directly or indirectly, are potentially useful in treating glaucoma, preventing tissue rejection in organ transplant patients, controlling nausea in patients undergoing chemotherapy, controlling pain and enhancing the appetite and controlling pain in individuals with AIDS Wasting Syndrome.

In addition to acting at the receptors, cannabinoids also affect cellular membranes, thereby producing undesirable side effects such as drowsiness, impairment of monoamine oxidase function and impairment of non-receptor mediated brain function. The addictive and psychotropic properties of cannabinoids also limit their therapeutic value.

Arachidonyl ethanolamide (anandamide) is an endogenous lipid that binds to and activates cannabinoid receptors and mimics the pharmacological activity of $\Delta^9$THC. In general, anandamide has been found to be somewhat less potent than $\Delta^9$THC. Despite having a rapid onset of action, the magnitude and duration of action of anandamide is relatively short, presumably because of a rapid inactivation process consisting of carrier-mediated transport into cells followed by intra-cellular hydrolysis by a membrane-bound amidohydrolase, anandamide amidase. Thus, inhibitors of anandamide amidase have the effect of indirectly stimulating the receptors by increasing in vivo levels of anandamide. In this connection, attention is directed to Makriyannis et al U.S. Pat. Nos. 5,688,825 and 5,874,459, the disclosures of which are incorporated herein by reference.

Anandamide released by depolarized neurons is believed to be subject to rapid cellular uptake followed by enzymatic degradation. Indeed, rat brain neurons and astrocytes in primary culture avidly take up radioactively labeled anandamide through a mechanism that meets four key criteria of a carrier-mediated transport; temperature dependence, high affinity, substrate selectivity, and saturation. In that other lipids including polyunsaturated fatty acids and prostaglandin $E_2$ ($PGE_2$) enter cells by carrier-mediated transport, it is possible that anandamide uses a similar mechanism. This accumulation may result from the activity of a transmembrane carrier or transporter, which may thus participate in termination of the biological actions of anandamide. This carrier or anandamide transporter is believed to be involved in the inactivation of anandamide. Thus, anandamide released from neurons on depolarization may be rapidly transported back into the cells and subsequently hydrolyzed by an amidase thereby terminating its biological actions. Consequently, the anandamide transporter is a potential therapeutic target for the development of useful medications.

There is considerable interest in understanding the mechanism of anandamide transport and in developing pharmacological agents that selectively interfere with it. Anandamide transport inhibitors may be used as experimental tools to reveal the possible physiological functions of this biologically active lipid. Many of these functions are still elusive despite a growing body of evidence suggesting that the endocannabinoid system is intrinsically active not only in brain and spinal cord, but also in peripheral tissue. Furthermore, anandamide transport inhibitors may offer a rational therapeutic approach to a variety of disease states, including pain, psychomotor disorders, and multiple sclerosis, in which elevation of native anandamide levels may bring about a more favorable response and fewer side effects than direct activation of CB1 receptors by agonist drugs.

SUMMARY OF THE INVENTION

It has now been found that certain analogs of anandamide are potent inhibitors of transport of anandamide across cell membranes. The transport inhibitor does not activate the cannabinoid receptors or inhibit anandamide hydrolysis per se but instead prevents anandamide reuptake thereby prolonging the level of the undegraded anandamide. Previously, cannabinoid drugs were targeted toward cannabiniod receptors and amidase enzymes. The anandamide transport inhibitor of the present invention targets activity of the anandamide transporter.

The inhibitors are amide and ester analogs of anandamide and exhibit the tail, central and head pharmacophore portions represented by Structural Formula I

$$X—Y—Z \qquad (I)$$

wherein tail portion X is a fatty acid chain remnant, central portion Y is an amide or ester radical and head portion Z is selected form the group consisting of hydrogen, alkyl, hydroxy alkyl, aryl, hydroxy aryl, heterocyclic and hydroxy heterocyclic radicals.

The novel inhibitors of the present invention, when tested in vitro, inhibit accumulation of anandamide in rat cortical neurons and astrocytes and enhance various effects of anandamide administration both in vitro and in vivo. The vasodepressor responses are significantly potentiated and prolonged by the transport inhibitors. Thus, the inhibitors are believed to be effective drugs for the treatment of cardivascular diseases and blood pressure disorders.

The novel biochemical pathway involving the anandamide transporter system and composition disclosed herein have other therapeutic uses. For example, the compounds and methods of the present invention, like cannabinoids, can be effective in the relief of the pain caused by cancer and the nausea resulting from cancer chemotherapy. Beneficially, they would not be expected to have the undesirable membrane-related side-effects associated with cannabinoids. In addition, the methods and compounds disclosed herein may be immunosuppressive and can therefore be used to prevent organ rejection in an individual undergoing an organ transplant. Because the compounds and methods of the present invention enhance the appetite of an individual, they can be used to treat patients with AIDS Wasting Syndrome, who are often suffering from malnourishment as a result of appetite loss. The compounds could also be used to combat Kinetic disorders and peripheral hypertension.

The novel inhibitors of anandamide transport disclosed herein also have research uses. For example, they can be used to maintain the level of anandamide in vivo to study the effect of anandamide on individuals and animals. The anandamide transport inhibitors disclosed herein can also be used as an aid in drug design, for example as a control in assays for testing other compounds for their ability to inhibit anandamide transport and to determine the structural and activity requirements of such inhibitors. These results, together with data from initial experiments on the selectivity of radioactively labeled [$^3$H]anandamide uptake by rat brain astrocytes, suggest that the interactions of anandamide with its putative transporter protein are governed by strict structural requirements. These results delineate the broad molecular requisites for this process, thus providing a basis for the design of more potent and selective inhibitors with potential applications to medicine.

Anandamide uptake in neurons and astrocytes has been found to be mediated by a high-affinity, Na$^+$-independent transporter that is selectively inhibited by the inhibitors of the present invention. The structural determinants governing recognition and translocation of substrates by the anandamide transporter have been determined. The results show that substrate recognition by the transporter is favored by a polar nonionizable head group of defined stereochemical configuration containing a hydroxyl moiety at its distal end. The secondary amido group interacts favorably with the transporter, but may be replaced with either a tertiary amide or an ester, suggesting that it may serve as hydrogen acceptor. Putative endogenous cannabinoid esters also serve as a substrate for the transporter. Substrate recognition and translocation require the presence of at least one cis double bond situated at the middle region of the fatty acid hydrocarbon chain, indicating a preference for ligands whose hydrophobic tail can adopt a bent U-shaped or hair-pin configuration. Uptake experiments with radioactively labeled substrates favor two or more and preferably four cis nonconjugated double bonds for optimal translocation across the cell membrane, suggesting that substrates are transported in a folded hairpin conformation.

DETAILED DESCRIPTION OF THE INVENTION

Figure 1:
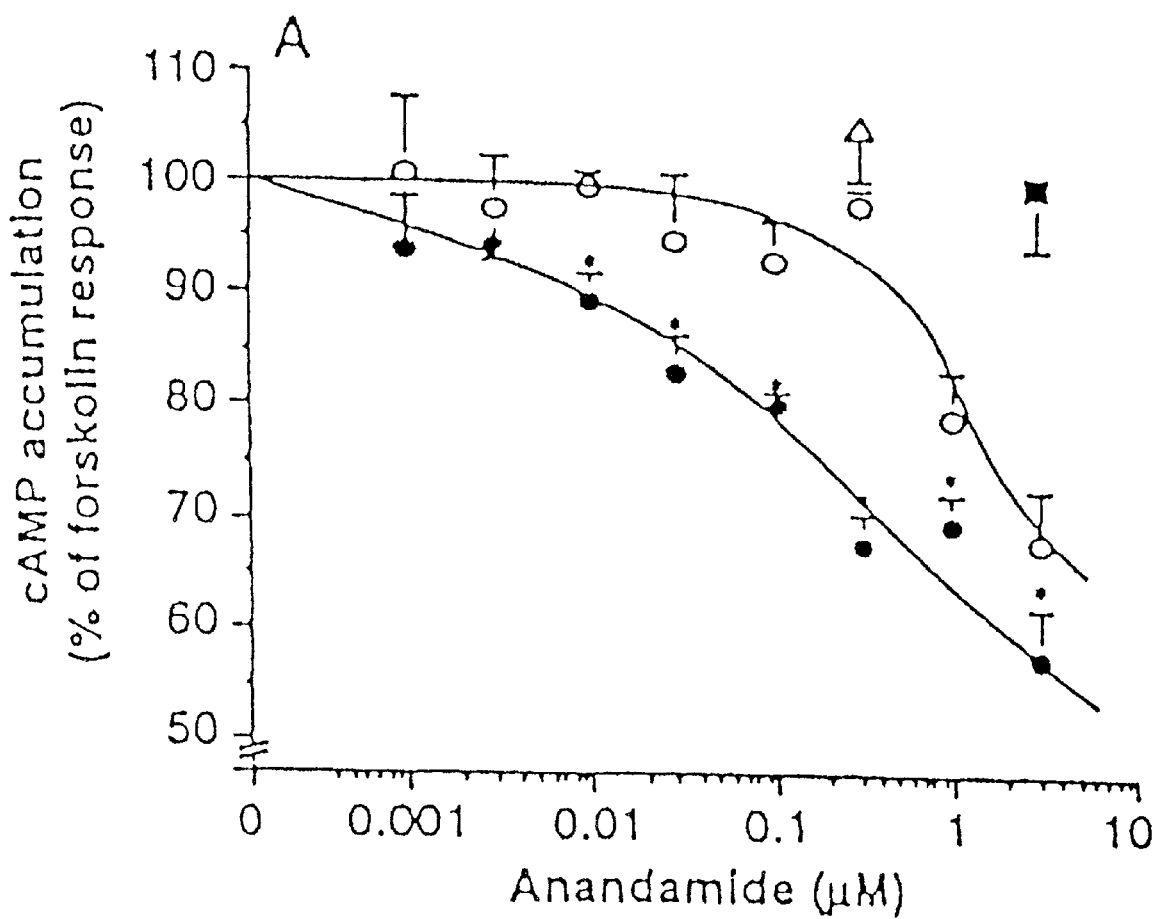
FIG. 1 is a graph showing the effect on adenylyl cyclase activity in the presence of anandamide alone and in combination with the transporter inhibitor.

One embodiment of the present invention is directed to the discovery of a putative anandamide transporter system which can be used as a target for the discovery of novel medications. These would include all compounds that can inhibit the function of this transporter. The invention further includes the pharmacological formula containing an effective amount of the inhibitor while another embodiment is directed to a method of inhibiting anandamide transport in an individual or animal by administering a therapeutically effective amount of the inhibitor and/or physiologically acceptable salts thereof. The inhibition results in increased levels of anandamide in the individual or animal, thereby causing prolonged stimulation of cannabinoid receptors in the individual or animal, e.g., the CB1 receptor in the brain and the CB2 receptor in the spleen. Thus, the present invention involves not only the inhibitor itself but also a method of reducing anandamide transporter activity in an individual or animal. It is to be understood that the present invention may also be used to reduce the activity of transporters not yet discovered for which anandamide and/or a cannabinoid act as an agonist.

The anandamide transport inhibitors of the present invention are amide and ester analogs of anandamide having the three pharmacophores of the Structural Formula I wherein the tail portion X is a fatty acid hydrophobic carbon chain having one or more nonconjugated cis double bonds in the middle portion of the aliphatic hydrocarbon chain. The chain may contain four to thirty carbon atoms but preferably the chain length is about 10 to 28 carbon atoms and more preferably contains from about 17 to about 22 carbon atoms. By contrast, analogs with fully saturated chains or with a trans or terminal double bond fail to compete successfully with [$^3$H]anandamide for transport and thus are ineffective as inhibitors. The central pharmacophore Y is selected from the group consisting of amide and ester radicals. Conversely, compounds containing a free carboxylic acid, carboxyethyl and carboxymethyl groups, or a primary alcohol are inactive. The head portion Z is selected from the group consisting of hydrogen, lower alkyl, hydroxy substituted lower alkyl, aryl, hydroxy substituted aryl, heterocyclic and hydroxy substituted heterocyclic radicals.

As used herein, "aliphatic hydrocarbon" includes one or more polyalkylene groups connected by one or more cis-alkenyl linkages such that the total number of methylene carbon atoms is within the ranges set forth herein. The structure of preferred tail portions have the formula II $$CR_3-(CR_2)_a-(cis-CH=CHCrR_2)_b-(CR_2)_c- \quad (II)$$

wherein R is selected from the groups consisting of hydrogen and lower alkyl groups, a and c are integers 0 and 1 through 10 and b is an integer from 1 through 6. Specific examples include structures where X is $CH_3-(CH_2)_4$-(cis-CH=CHCH$_2-)_4-(CH_2)_2-$, $CH_3-(CH_2)_4$-(cis-CH=CHCH$_2)_3-(CH_2)_5$, $-CH_3-(CH_2)_6$-(cis-CH=CHCH$_2)_2-(CH_2)_6-$, $CH_3-(CH_2)_6$-(cis-CH=CHCH$_2)_2-(CH_2)_5$ $-CH_3-(CH_2)_7$-cis CH=CH$-$(CH$_2)_9$, $CH_3-(CH_2)_7$-cis-CH=CH$-$(CH$_2)_7-$ and $CH_3-$(CH$_2)_4-$(CH=CHCH$_2)_4-$CH$_2-$C(CH$_3)_2-$. A lower alkyl group is a straight or branched chain alkyl group having 1 to 5 carbon atoms.

As used herein, an "aryl" group is a carbocyclic aromatic ring system such as phenyl, 1-naphthyl or 2-naphthyl.

As used herein, a "heterocyclic" group is a non-aromatic ring system of 4 to 8 carbon atoms containing one or more heteroatoms such as oxygen or nitrogen with the amido nitrogen forming part of the ring structure. Examples include pyrrolidinyl and piperidinyl groups.

All amides may be synthesized by the reaction of the fatty acid or fatty acid halide, such as the chloride, with the appropriate amine or aminoalcohol as described in Abadjj et al, *J. Med. Chem.*, 37, 1889-93 (1994) while all esters may be synthesized by the reaction with the appropriate alcohols. 1- and 2-arachidonylglycerols may be prepared by a modification of the procedure established by Serdarevich et al, *J. Lipid Res.*, 7, 277 (1966) for the synthesis of fatty acid monoglycerides. Radioactively labeled fatty acid ethanolamides may be prepared by the reaction of acid chlorides (Nu-Check Prep, Elysian, Minn.) with [$^3$H]ethanolamine (10-30 Ci/mmol; American Radiolabeled Chemicals, St. Louis) as described in Desarnad, *J. Biol. Chem.*, 270, 6030 (1995). All compounds may be purified by HPLC or flash column chromatography, and their identities may be established by NMR and/or gas chromatography-mass spectrometry. Exploration of the Y and Z pharmacophores shows that compounds containing primary, secondary and tertiary amido groups as well as hydroxyethyl ester or glycerol ester moieties are capable of competing with [$^3$H]anandamide, but exhibit a wide range of potencies. Structural variations of the head group Z leads to analogs with diverse selectivities for the anandamide transporter. Thus substitution of the terminal hydroxyl with a hydrogen causes a substantial decrease in potency, whereas replacement of the entire hydroxyalkyl moiety with hydrogen yields compounds that are as potent as anandamide. Introduction of a methyl group alpha to the amido nitrogen also leads to active compounds. Chiral molecules display considerable enantioselective inhibition of [$^3$H]anandamide transport. The (S) enantiomer is approximately four times more potent than its (R) isomer.

To study the effects of head group conformational preference, a set of analogs was prepared in which the head group is partially restricted by incorporation into five- or six-member rings. The resulting 3- and 4-hydroxypiperidinyl- and 3-hydroxypyrrolidinyl-amides, which were tested as racemic pairs, have activities for the transporter similar to that of anandamide. Another cyclic head group analog, having both the amido nitrogen and an ether oxygen restricted into a morpholine ring maintains considerable activity (approximately half that of anandamide), indicating that the hydrogen in the hydroxyl head group may not be necessary for interaction with the transporter.

The most striking structure-activity correlation was observed with analogs having hydroxyphenyl radicals at the head group. Use of the hydroxyphenyl group leads to relatively potent uptake inhibitors, with the 4-hydroxyphenyl analog being distinctly the most successful. Conversely, the 4-methylphenyl analog as well as other analogs with electron donating or electron withdrawing para substituents display no significant activity. Varying these substituents from the para to the meta or ortho position does not restore activity. Other analogs containing multiple substituents on the phenyl ring (e.g., 3-chloro-4-hydroxyphenyl) or a bulkier aromatic moiety [e.g., 1-(4-hydroxynaphthyl)] are also less potent than the 4-hydroxyphenyl group.

The Transporter.

In order to properly evaluate the effectiveness of inhibitors of anandamide transport, it was necessary to establish the identity and character of the carrier-mediated transporter. The accumulation of radioactively labeled exogenous [$^3$H]anandamide by neurons and astrocytes fulfills several criteria of a carrier-mediated transport. It is a rapid process that reaches 50% of its maximum within about four minutes. Furthermore, [$^3$H]anandamide accumulation is temperature dependent and saturable. Kinetic analyses reveals that accumulation in neurons can be represented by two components of differing affinities (lower affinity: Michaelis constant, $K_m$=1.2 µM, maximum accumulation rate, $V_{max}$=90.9 pmol/min per milligram of protein; higher affinity: $K_m$=0.032 µM, $V_{max}$=5.9 pmol/min per milligram of protein). The higher affininy component may reflect a binding site, however, as it is displaced by the cannabinoid receptor antagonist, SR-141716-A (100 nM). In astrocytes, [$^3$H]anandamide accumulation is represented by a single high-affinity component ($K_m$=0.32 µM, $V_{max}$=171 pmol/min per milligram of protein). Such apparent $K_m$ values are similar to those of known neurotransmitter uptake systems and are suggestive therefore of high-affinity carrier-mediated transport.

To characterize further this putative anandamide transporter, cortical astrocytes in culture were employed. As expected from a selective process, the temperature-sensitive component of [$^3$H]anandamide accumulation was prevented by nonradioactive anandamide, but not by palmitoyl ethanolamide, arachidonate, prostanoids, or leukotrienes. Replacement of extracellular sodium ion with N-dimethylglocosamine or choline had no effect suggesting that accumulation is mediated by a $Na^+$-independent mechanism which has been observed for other lipids. Moreover, inhibition of fatty acid amide hydrolase (FAAH) activity indicates that an anandamide hydrolysis does not provide the driving force for anandamide transport into astrocytes within the time frame of the experiment. Finally, the cannabinoid receptor agonist WIN-55212-2 (1 µM) and antagonist SR-141716-A (10 µM) also had no effect, suggesting that receptor internalization was not involved.

A primary criterion for defining carrier-mediated transport is pharmacological inhibition. To identify inhibitors of anandamide transport, examination was made of various components that prevent the cellular uptake of other lipids such as fatty acids, pholipholipids or bromcresol green. Among the compounds tested, only bromcresol green interfered with inanimate transport, albeit with limited potency and partial efficacy, bromcresol green inhibited [$^3$H]anandamide accumulation with an $IC_{50}$ (concentration needed to produce half-maximal inhibition) of 4 µM in neurons and 12 µM in astrocytes and acted noncompetitively. Moreover, bromcresol green had no significant effect on the binding of [$^3$H]WIN-55212-2 to rat cerebral membranes, on FAAH activity in brain microsomes and on uptake of [$^3$H]arachidonate or [$^3$H]ethanolamine in astrocytes.

The bromcresol green, which blocks $PGE_2$ transport, raised the question of whether anandamide accumulation occurred by means of a $PGE_2$ carrier. That this is not the case was shown by the lack of [$^3$H]$PGE_2$ accumulation in neurons or astrocytes and by the inability of $PGE_2$ to interfere with [$^3$H]anandamide accumulation. Previous results indicating that expression of $PGE_2$ transporter mRNA in brain tissue is not detectable further support this conclusion.

[$^3$H]anandamide Transport Assay.

For standard transport assays, confluent astrocytoma cells grown in 90-mm plates were incubated at 37° C. in 10 ml of Tris-Krebs' buffer containing $10\text{-}50\times10^6$ dpm/ml of the radioactive tracers of the test compounds (unless indicated otherwise, specific radioactivity was 0.31-0.69 mCi/mmol). At various times after the addition of tracer (0-20 min), 1-ml samples of the incubation media were collected for liquid scintillation counting. Under these conditions, clearance of radioactive material from the incubating medium provides an accurate estimate of transport into cells, as indicated both by previous work with rat brain neurons (2) and by preliminary experiments with astrocytoma cells.

The cells were incubated for 4 min at 37° C. in the presence of 10-500 nM anandamide containing 0.05-2.5 nM [$^3$H]anandamide. Nonspecific accumulation (measured at 0-4° C.) was subtracted before determining kinetic constants by Lineweaver-Burke analysis.

A minimum of three independent experiments conducted in triplicate was used to define the concentration needed to produce half-maximal inhibition ($IC_{50}$) for each compound. $IC_{50}$ values were obtained by nonlinear least-squares fitting of the data, using the PRIZM software package. All other experiments were carried out in triplicate and repeated at least twice with identical results. The formulae and IC$_{50}$ values of exemplary inhibitors are set forth in Table I with the first formula being anandamide and AA being the arachidonyl radical. Data are expressed as mean±SEM.

TABLE I

| Structure | IC$_{50}$ |
|---|---|
| (C20:4 ethanolamide) | 15.1 ± 3.0 |
| (C20:3 ethanolamide) | 13.0 ± 3.6 |
| (C20:2 ethanolamide) | 10.6 ± 1.5 |
| (C20:1 ethanolamide) | 14.1 ± 1.2 |
| (branched ethanolamide with C$_3$H$_7$) | 18.3 ± 4.2 |
| (C22:1 ethanolamide) | 10.5 ± 1.2 |
| AA-C(O)-NH-C$_2$H$_5$ | 48.5 ± 7.3 |
| AA-C(O)-NH$_2$ | 9 ± 2 |
| AA-C(O)-O-C$_4$H$_2$OH | 6.7 ± 0.8 |
| AA-C(O)-O-CH(OH)-CH$_2$OH | 18.5 ± 0.7 |
| AA-C(O)-O-CH$_2$-CH(OH)-CH$_2$OH | 48.5 ± 8.1 |

TABLE I-continued

| Structure | IC$_{50}$ |
|---|---|
| AA-C(O)-NH-CH(CH$_3$)-CH$_2$OH (R) | 37.7 ± 0.7 |
| AA-C(O)-NH-CH(CH$_3$)-CH$_2$OH (S) | 10.4 ± 1.2 |
| AA-C(O)-NH-C$_6$H$_4$-OH (para) | 2.2 ± 0.2 |
| AA-C(O)-NH-C$_6$H$_4$-OH (meta) | 21.3 ± 3.4 |
| AA-C(O)-N(morpholino) | 25 |
| AA-C(O)-N(4-hydroxypiperidinyl) | 10.0 ± 0.2 |
| AA-C(O)-N(3-hydroxypiperidinyl) | 15 |
| AA-C(O)-N(3-hydroxypyrrolidinyl) | 15.3 ± 3.0 |
| 2,2-dimethyl-AA-C(O)-NH-CH$_2$-CH$_2$OH | 7.6 ± 1.2 |
| 2,2-dimethyl-AA-C(O)-NH-CH$_2$-CH(OH)- (R) | 33.2 ± 4.2 |
| 2,2-dimethyl-AA-C(O)-NH-CH$_2$-CH(OH)- (S) | 16.5 ± 1 |

[$^3$H]Anandamide Transport in Astrocytoma Cells.

As expected of a carrier-mediated process, [$^3$H]Anandamide accumulation in human astrocytoma cells is rapid ($t_{1/2}$= 3 min), temperature dependent and saturable, displaying an apparent Michaelis constant ($K_m$) of 0.6±0.1 µM and a maximal accumulation rate ($V_{max}$) of 14.7±01.5 pmol/min per mg of protein (n=5). The accumulation is not affected by replacement of Na$^+$ with choline, indicating that it is mediated by a Na$^+$-independent mechanism. In addition, [$^3$H]anandamide accumulation is prevented by the anandamide transport inhibitor N-(4-hydroxyphenyl)-arachidonamide with a IC$_{50}$ value of 2.2±0.2 µM, whereas its positional isomer N-(3-hydroxyphenyl)-arachidonamide is 10 times less effective (IC$_{50}$=21.3±3.4).

Figure 4:
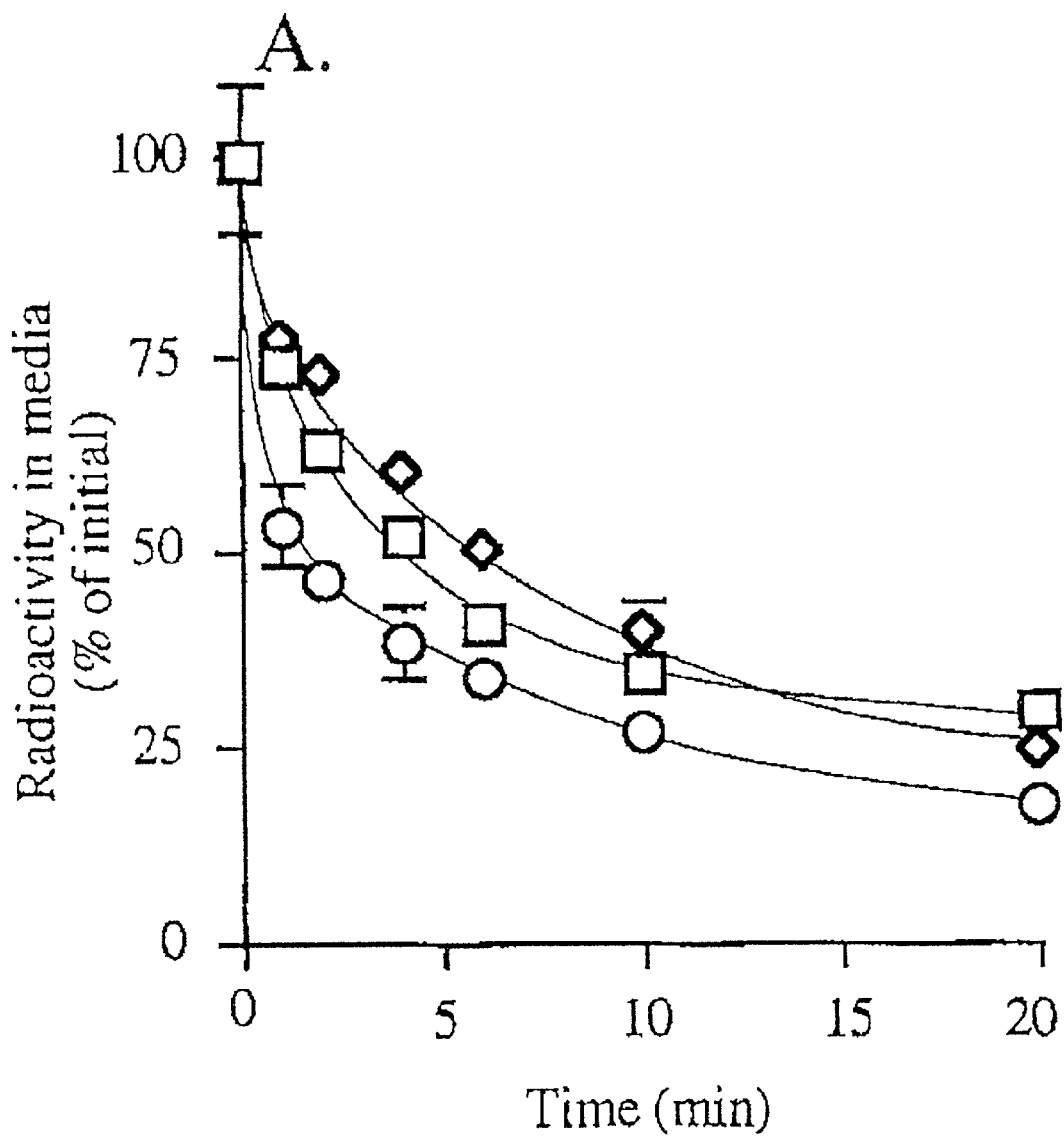
FIG. 4 is a graph showing the translocation of substrate inhibitors of the present invention.

Some of the inhibitors have been identified as competitive since they are recognized as substrates by the transporter and will undergo membrane translocation. The IC$_{50}$ data in Table I provide the affinity data for ligand recognition by the anandamide transporter, but do not provide information on whether the ligands also may serve as substrates for the transporter. To investigate substrate translocation we used a representative set of radioactively labeled compounds. We first tested three key analogs that compete with anandamide for uptake: [$^3$H]arachidonamide, [$^3$H]N-(4-hydroxyphenyl) arachidonamide, the most potent competitor in our series, and [$^3$H]2-arachidonylglycerol. As shown in FIG. 4, the [$^3$H]2-arachidonylglycerol (squares) and [$^3$H]N-(4-hydroxyphenyl) arachidonamide (diamonds) analogs are transported as rapidly and effectively as [$^3$H]anandamide (circles). These findings suggest that the anandamide transporter also may participate in the inactivation of 2-arachidonylglycerol, which was thought to be primarily mediated by enzymatic hydrolysis. In agreement with this possibility, kinetic analyses indicate that [$^3$H]2-arachidonylglycerol is accumulated in astrocytoma cells with an apparent $K_m$ of 0.7±0.1 µM and a $V_{max}$ of 28±6 pmol/min per mg of protein, values that are comparable to those obtained with [$^3$H]anandamide in the same cell preparation (n=3).

Figure 5:
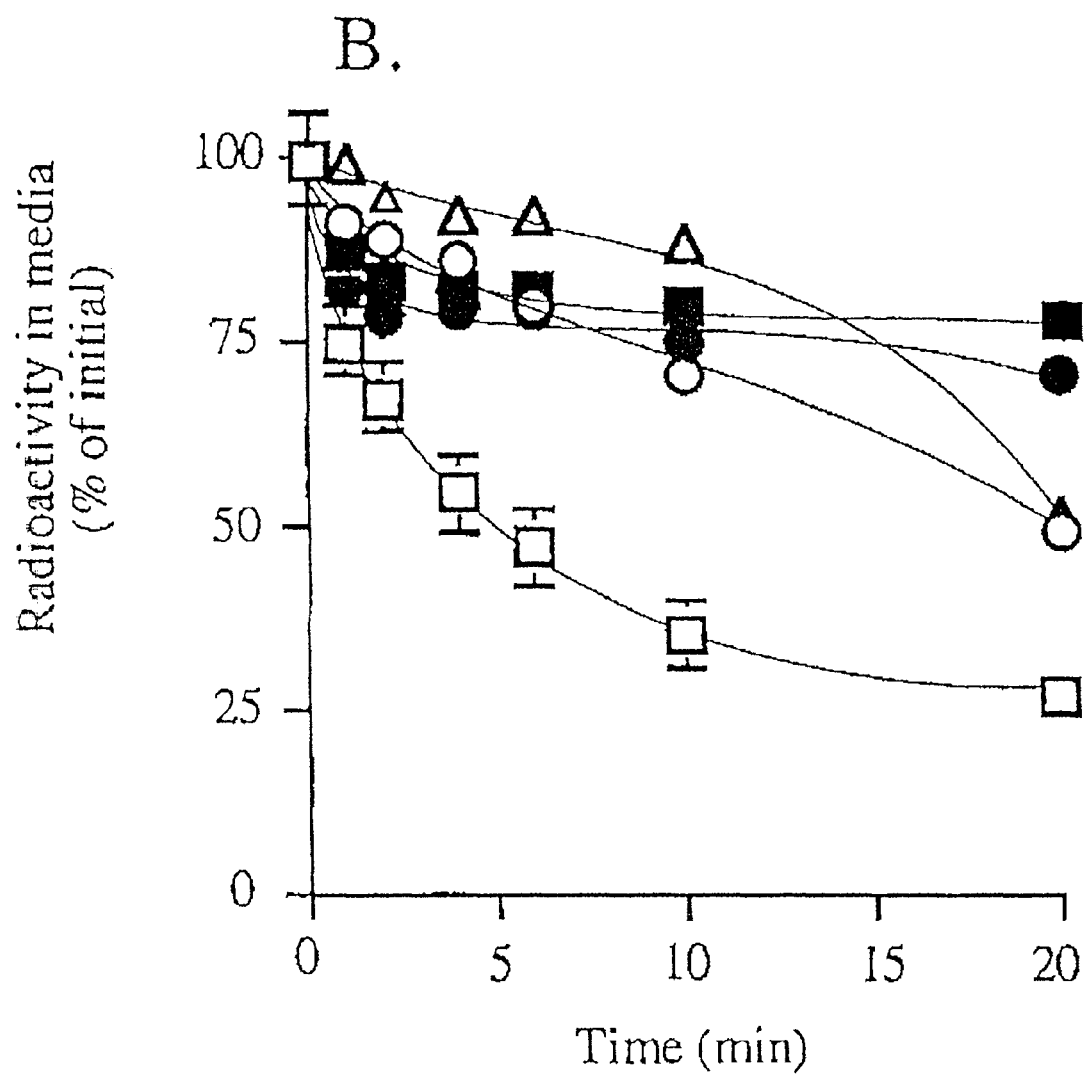
FIG. 5 is a graph showing the effect of the number of cis double bonds on translocation.

FIG. 5 shows the effects of modifications in the hydrophobic tail. In this study, in addition to [$^3$H]arachidonamide (empty squares), we tested one cis-triene analog [$^3$H]cis-eicosatrienoylethanolamide (empty circles) one cis-diene analog [$^3$H]cis-eicosadienoylethanolamide (triangles), and two cis monounsaturated analogs with the double bond located in the middle of the carbon chain, [$^3$H]cis-eicosaenoylethanoladide (full squares), and [$^3$H]oleylethanolamide (full circles). Although all of these fatty acid ethanolamides are able to compete with [$^3$H]anandamide for transport, only [$^3$H]arachidonamide is effectively transported into cells. Of the remaining compounds, the cis-triene and the cis-diene are transported very slowly ($t_{1/2}$≈20 min), whereas the two monoalkenes are not transported at all. [$^3$H]Palmitylethanolamide, a saturated acid ethanolamide that may activate an as-yet-uncharacterized peripheral CB2-like receptor, is not transported to any significant extent. These findings indicate the existence of two distinct sets of structural requirements in the function of the anandamide transporter, one for substrate recognition and another fro substrate translocation.

Modifications of the hydrophobic fatty acid tail reveal unexpectedly distinct requirements for recognition and translocation of substrates by the anandamide transporter. Substrate recognition requires the presence of at least one cis double bond situated at the middle of the fatty acid chain, pointing to a preference for ligands in which the hydrophobic tail can fold in the middle and adopt a bent U-shaped conformation. Indeed, analogs with fully saturated chains or those incorporating trans double bonds do not interact significantly with the transporter. By contrast, sustrate translocation requires a minimum of four cis nonconjugated double bonds, as ligands containing one, two, or three olefins are transported either very slowly or not at all. This finding suggests that for transmembrane transport to occur substrates must be capable of adopting a tightly folded conformation, one that is not energetically favorable for ligands containing an insufficient number of cis double bonds.

Molecular modeling studies of fatty acid ethanolamides differing in the degree of unsaturation of their hydrophobic carbon chains provides insight into these distinctive conformational requirements. Possible low-energy conformers of these molecules are significantly different. The presence of one or more nonconjugated cis double bonds in the middle of the chain leads to the formation of a turn that brings in closer proximity the head and tail of the molecule. The shape of this turn is determined by the number and position of the cis double bonds. Conversely, the introduction of a central trans double bond yields a more extended chain conformation and hinders the ability of the molecule to undergo folding. Thus one of the low-energy conformers of anandamide displays a folded hairpin shape with the two halves of the molecule facing each other. The cis-triene analog may adopt an analogous conformation, though one that is wider than that of anandamide. The width of the turn increases considerably in the cis-dienes and the two monoalkenes due to the marked increase in distance between the head group and tail of the molecule. In the corresponding trans alkene analog, the distance between the head and tail is much greater. It is important to point out that, whereas anandamide like arachidonic acid may adopt either a closed-hairpin or a U-shaped conformation depending on the properties of the surrounding milieu, the hairpin conformation may be thermodynamically unfavorable to fatty acid ethanolamides containing only one or two double bonds.

A plausible interpretation of our results is that recognition and translocation of substrates by the anandamide transporter are governed by distinct conformational preferences. Although the initial recognition step may require that substrates assume a bent U-shaped conformation of variable width, the subsequent step of translocation across the cell membrane may impose a more tightly folded hairpin conformation.

A "therapeutically effective amount" of a compound, as used herein, is the quantity of a compound which, when administered to an individual or animal, results in a sufficiently high level of anandamide in the individual or animal to cause a discernable increase or decrease in a cellular activity affected or controlled by cannabinoid receptors. For example, anandamide can stimulate receptor-mediated signal transduction that leads to the inhibition of forskolin-stimulated adenylate cyclase (Vogel et al., *J. Neurochem.* 60:352 (1993)). Anandamide also causes partial inhibition of N-type calcium currents via a pertussis toxin-sensitive G protein pathway, independently of cAMP metabolism (Mackie et al., *Mol. Pharmacol.* 47:711 (1993)).

A "therapeutically effective amount" of an anandamide inhibitor can also be an amount which results in a sufficiently high level of anandamide in an individual or animal to cause a physiological effect resulting from stimulation of cannabinoid receptors. Physiological effects which result from cannabinoid receptor stimulation include analgesia, decreased nausea resulting from chemotherapy, sedation and increased appetite. Other physiological functions include relieving intraocular pressure in glaucoma patients and suppression of the immune system. Typically, a "therapeutically effective amount" of the compound ranges from about 10 mg/day to about 1,000 mg/day.

As used herein, an "individual" refers to a human. An "animal" refers to veterinary animals, such as dogs, cats, horses, and the like, and farm animals, such as cows, pigs, guinea pigs and the like.

The compounds of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular or subcutaneous administration and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles may include saline, sterile water, Ringer's solution, and isotonic sodium chloride solutions. The specific dosage level of active ingredient will depend upon a number of factors, including, for example, biological activity of the particular preparation, age, body weight, sex and general health of the individual being treated.

EXAMPLE 1

Effects of N-(4-hydroxyphenyl)-arachidonamide on Anandamide-Induced Inhibition of Adenylyl Cyclase Activity in Cortical Neurons Cortical neurons were prepared in 12-well plates and used after 4 to 6 days in vitro. Incubations were carried out in the presence of forskolin (3 μM) and isobutyl methyl zanthine (1 mM). The cAMP concentrations were measured by radioimmunoassay with a commercial kit (Amersham, Arlington, Ill.) and following manufacturer's instructions. FIG. 1 reports the results when the neurons were stimulated with forskolin (3 μM) in the presence of anandamide (0.001 to 3 μM; open circles), anandamide (0.001 to 3 μM) plus inhibitor N-(4-hydroxyphenyl)-arachidonamide (10 μM) (filled circles), anandamide (3 μM) plus SR-141716-A (1 μM) (square), or anandamide (0.3 μM) plus the inhibitor (10 μM) and SR-141716-A (1 μM) (triangle).

EXAMPLE 2

Figure 2:
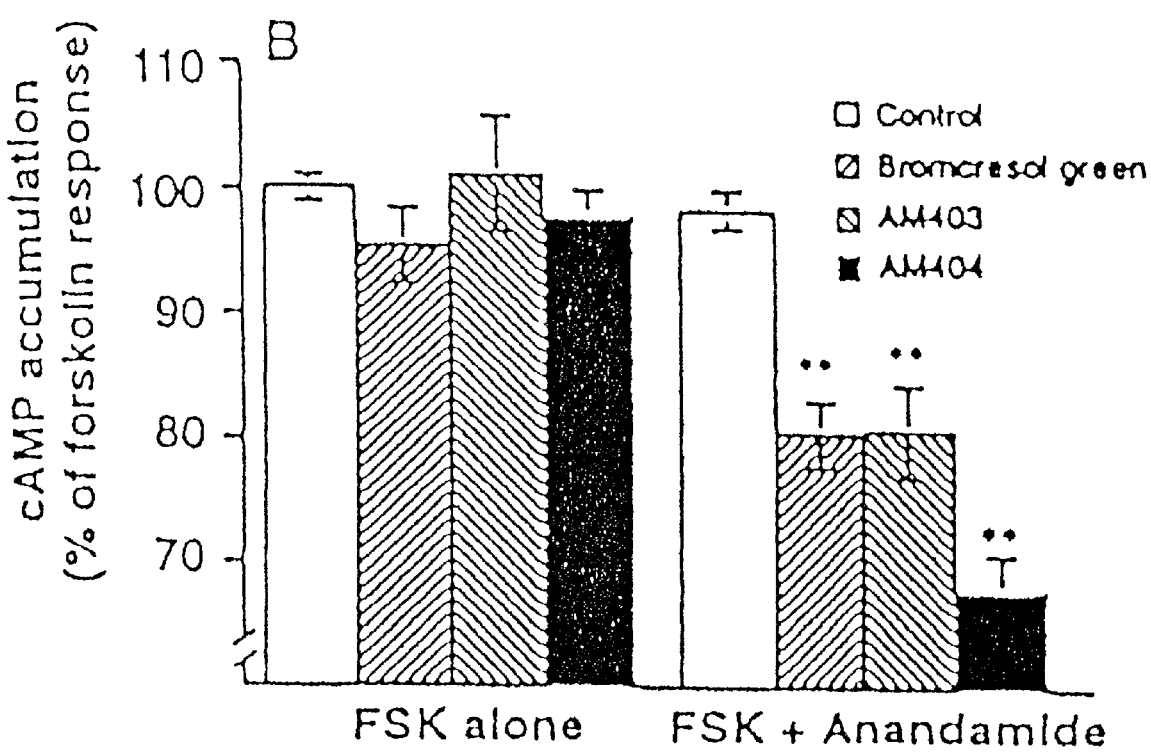
FIG. 2 is a graph showing the effect of anandamide transport inhibitors on adenylyl cyclase activity.

Effects of Anandamide Aransport Inhibitors on Anandamide-Induced Inhibition of Adenylyl Cyclase Activity Forskolin (FSK)-stimulated neurons were separately incubated with inhibitors N-(4-hydroxyphenyl)-arachidonamide, (Sample AM404), N-(3-hydroxyphenyl)-arachidonamide (Sample AM403), and bromcresol green (each at 10 μM) without (FSK alone) or with (FSK+anandamide) 0.3 μM anandamide. The results are shown in FIG. 2, expressed as mean±SEM of nine independent determinations. One asterisk indicates P<0.05 and two asterisks P<0.01 (ANOVA followed by Bonferoni test).

The amount of cAMP in the presence of a concentration of WIN-55212-2 below threshold (1 nM, determined in preliminary experiments) were 96.7±2.5% of forskolin alone and were not significantly affected by 10 μM of 404 (89.8±2.6%), 10 μM of 403 (92.4±2.3%), or 10 μM bromcresol green (92.9±2.3%) (n=3). In the presence of a concentration of glutamate below the threshold (3 μM), cAMP concentrations were 91.6±2% of forskolin alone and were not significantly affected by 404 (84.4±4.9%), 403 (89.5±2,4%), or bromcresol green (84.4±3%) (n=3).

The transport inhibitor AM404 bound to CB1 receptors with low affinity ($K_i$=1.8 μM) and did not reduce cAMP concentrations when applied at 10 μM. Nevertheless, the drug enhanced the effects of anandamide, increasing the potency (by a factor of 10) and decreasing the threshold (by a factor of 1.100), an effect that was prevented by SR-141716-A. Thus, a concentration of anandamide that was below threshold when applied alone (0.3 μM) produced an almost maximal effect when applied with AM404. Bromcresol green and inhibitor AM403, which were less effective than AM404 in inhibiting anandamide transport, were also less effective in enhancing the anandamide response. Furthermore, the decreases in cAMP concentrations produced by WIN-55212-2 (which stimulates CB1 receptors but is not subject to physiological clearance) or glutamate (which stimulates metabotropic receptors negatively coupled to adenylyl cyclase and is cleared by a selective transporter) are not affected by any of the anandamide transport inhibitors tested.

EXAMPLE 3

Effects of Sample AM404 on the Analgesic Activity of Anandamide in the Hot Plate Test.

The hot plate test (55.5° C.) was carried out on male Swiss mice (25 to 30 g, Nossan, Italy) followed standard procedures [F. Porreca, H. L. Mosberg, R. Hurst, V. J. Hruby, T. F. Burke, *J. Pharmacol. Exp. Ther.* 230, 341 (1994)]. Anandamide and AM404 were dissolved in 0.9% NaCl solution containing 20% dimethyl sulfoxide and injected intravenously at 20 mg/kg and 10 mg/kg, respectively. To determine whether cannabinoid receptors participate in the effect of anandamide, we administered anandamide (20 mg/kg, subcutaneously) to two groups of six mice each. In mice that received anandamide alone, latency to jump increased from 21.7±1.5 s to 30.7±0.8 s (P<0.05, ANOVA) 20 min after injection. In contrast, in mice that received anandamide plus SR141716-A, the latency to jump was not affected (19.5±3.1 s).

Figure 3:
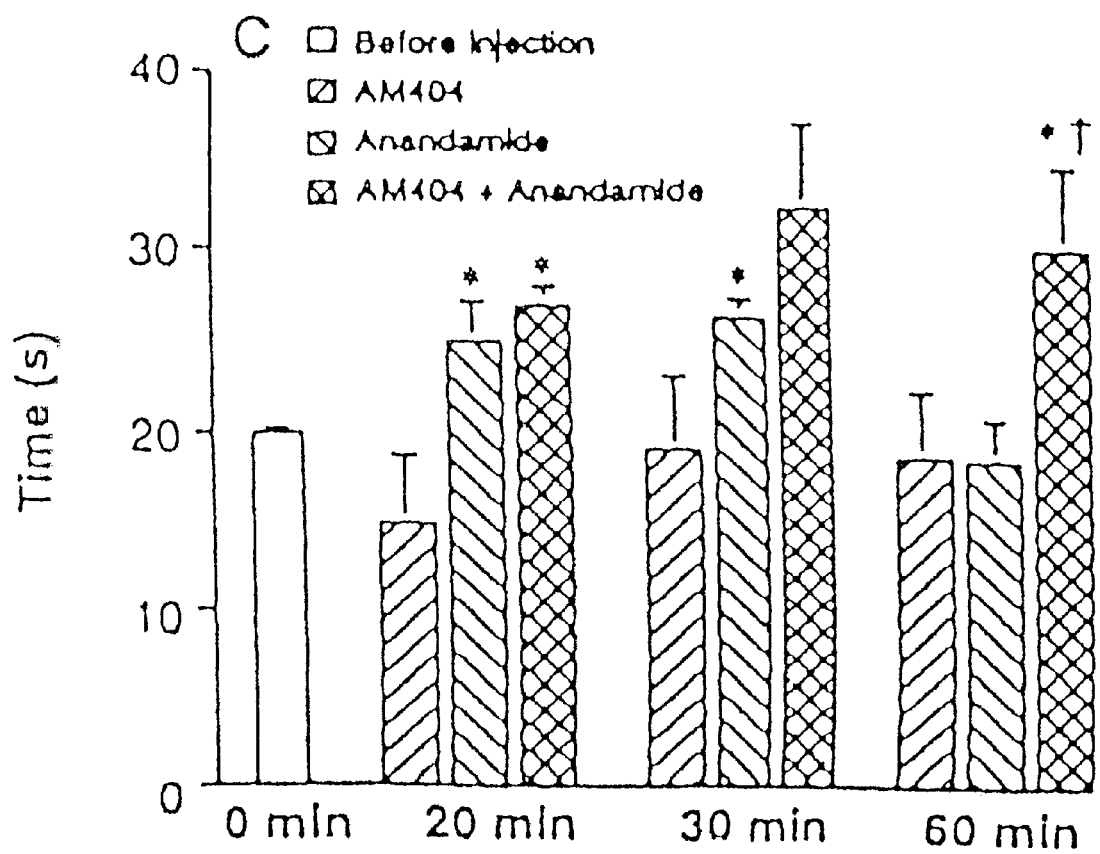
FIG. 3 is a graph showing the effect of the transporter inhibitor on the analgesic activity of anandamide in the hot plate test.

Three groups of six mice received Sample 404 (10 mg/kg, intravenous), anandamide (20 mg/kg, intravenous), or anandamide plus 404. The hot plate test (55.5° C.) was performed at the times indicated, and latency to jump (in seconds) was measured before (control) and after the drugs were injected. In all groups, latency to jump before injections was 21±0.6 s (n=18). A fourth group of mice received injections of vehicle alone (saline containing 20% dimethyl sulfoxide), which did not affect latency to jump. One asterisk indicates P<0.05 compared with uninjected controls (ANOVA followed by Bonferroni test), and one cross indicates P<0.01 compared with anandamide-treated animals (Student's t test). Results are set forth in FIG. 3.

Intravenous anandamide (20 mg. per kilogram of body weight) elicited a modest but significant analgesia, as measured by the hot plate test (P<0.05 Student's t test); this analgesia disappeared 60 min after injection and was prevented by SR-14171 6-A. Administration of AM404 (10 mg/kg, intravenously) had no antinociceptive effect within 60 min of injection but significantly enhanced and prolonged anandamide-induced analgesia (P<0.01, Student's t test).

Those skilled in the art will recognize, or be able to ascertain using no more than routine experimentation, many equivalents to specific embodiments of the invention described specifically herein. Such equivalents are intended to be encompassed in the scope of the invention.

The invention claimed is:

1. A method of inhibiting transport of anandamide in an individual or animal comprising administering to the individual or animal a pharmacological preparation comprising a therapeutically effective amount of a compound represented by the following structural formula and physiologically acceptable salts thereof:

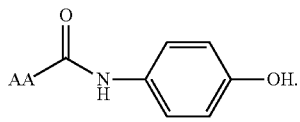

2. The method of claim 1 wherein the compound is in purified form.

3. The method of claim 1 wherein the pharmacological preparation further comprises at least one member selected from a vehicle, an adjuvant, a flavoring, a colorant, or a preservative and the compound is in purified form.

4. A method of inhibiting transport of anandamide in an individual or animal comprising administering to the individual or animal a therapeutically effective amount of a pharmacological preparation comprising a compound represented by the following structural formula and physiologically acceptable salts thereof

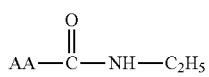 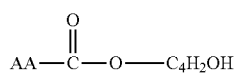

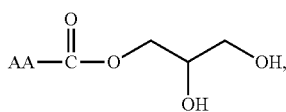

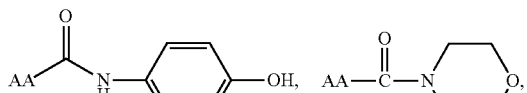

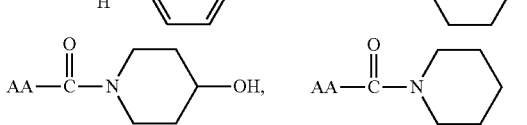

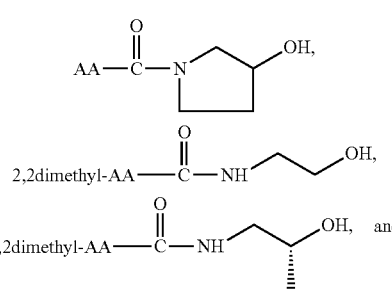

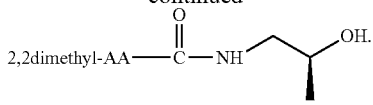

5. The method of claim 4 wherein the compound is represented by the following structural formula and physiologically acceptable salts thereof:

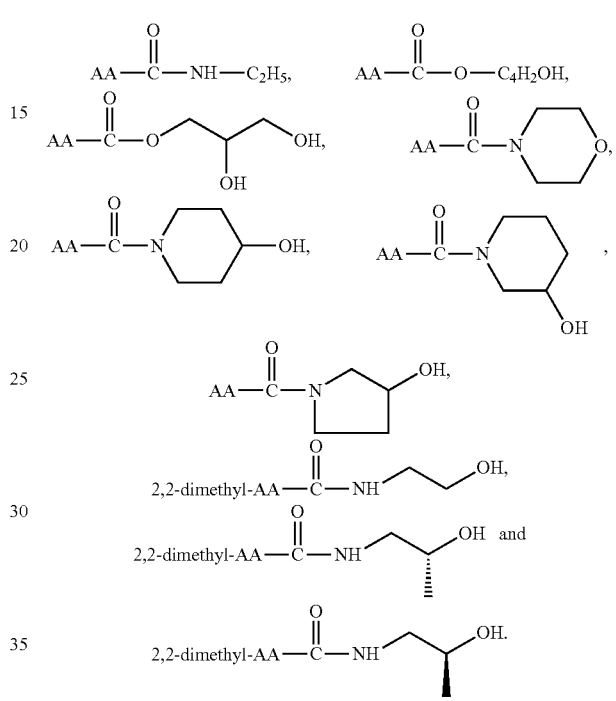

6. The method of claim 4 wherein the compound is represented by the following structural formula and physiologically acceptable salts thereof:

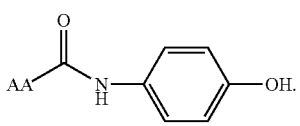

7. The method of claim 5 wherein the compound is in purified form.

8. The method of claim 5 wherein the pharmacological preparation further comprises at least one member selected from a vehicle, an adjuvant, a flavoring, a colorant, or a preservative and the compound is in purified form.

9. The method of claim 4 wherein the compound is in purified form.

10. The method of claim 4 wherein the pharmacological preparation further comprises at least one member selected from a vehicle, an adjuvant, a flavoring, a colorant, or a preservative and the compound is in purified form.

* * * * *